United States Patent
Sharma et al.

(10) Patent No.: US 11,097,018 B2
(45) Date of Patent: Aug. 24, 2021

(54) ORGANOMEDICINALS FOR IMAGING AND TREATMENT OF NEURODEGENERATIVE DISORDERS

(71) Applicant: Washington University, St. Louis, MO (US)

(72) Inventors: Vijay Sharma, St. Louis, MO (US); Jothilingam Sivapackiam, St. Louis, MO (US); Sundaram S. M. Guruswami, St. Louis, MO (US)

(73) Assignee: Washington University, St. Louis, MO (US)

( * ) Notice: Subject to any disclaimer, the term of this patent is extended or adjusted under 35 U.S.C. 154(b) by 0 days.

(21) Appl. No.: 16/123,845

(22) Filed: Sep. 6, 2018

(65) Prior Publication Data
US 2019/0070320 A1 Mar. 7, 2019

Related U.S. Application Data

(60) Provisional application No. 62/554,865, filed on Sep. 6, 2017.

(51) Int. Cl.
| | |
|---|---|
| *A61K 51/04* | (2006.01) |
| *A61P 25/28* | (2006.01) |
| *C07D 277/66* | (2006.01) |
| *C07D 215/22* | (2006.01) |
| *A61K 31/375* | (2006.01) |
| *C07D 215/38* | (2006.01) |
| *C07D 277/64* | (2006.01) |
| *A61K 31/343* | (2006.01) |
| *A61K 45/06* | (2006.01) |
| *A61K 31/436* | (2006.01) |

(52) U.S. Cl.
CPC ...... *A61K 51/0453* (2013.01); *A61K 51/0455* (2013.01); *A61P 25/28* (2018.01); *C07D 215/22* (2013.01); *C07D 215/38* (2013.01); *C07D 277/64* (2013.01); *C07D 277/66* (2013.01); *A61K 31/343* (2013.01); *A61K 31/375* (2013.01); *A61K 31/436* (2013.01); *A61K 45/06* (2013.01); *A61K 2300/00* (2013.01)

(58) Field of Classification Search
CPC ....... A61P 25/28; A61K 51/04; A61K 31/343; A61K 31/375; C07D 215/22; C07D 277/66
See application file for complete search history.

(56) References Cited

U.S. PATENT DOCUMENTS

| | | |
|---|---|---|
| 4,241,046 A | 12/1980 | Papahadjopoulos et al. |
| 4,394,448 A | 7/1983 | Szoka, Jr. et al. |
| 4,529,561 A | 7/1985 | Hunt et al. |
| 4,755,388 A | 7/1988 | Heath et al. |
| 4,828,837 A | 5/1989 | Uster et al. |
| 4,925,661 A | 5/1990 | Huang |
| 4,954,345 A | 9/1990 | Muller |
| 4,957,735 A | 9/1990 | Huang |
| 5,043,164 A | 8/1991 | Huang et al. |
| 5,064,655 A | 11/1991 | Uster et al. |
| 5,077,211 A | 12/1991 | Yarosh |
| 5,264,618 A | 11/1993 | Felgner et al. |

FOREIGN PATENT DOCUMENTS

| | | | | |
|---|---|---|---|---|
| WO | WO-2015051188 A1 | * | 4/2015 | ......... A61K 51/0459 |
| WO | WO 2015051188 | * | 9/2015 | |

OTHER PUBLICATIONS

Abbas, A. et al., "Molecular Linker-Mediated Self-Assembly of Gold Nanoparticles: Understanding and Controlling the Dynamics," Langmuir, Jan. 2013, pp. 56-64, vol. 29, No. 1.

* cited by examiner

*Primary Examiner* — Michael G. Hartley
*Assistant Examiner* — Jagadishwar R Samala
(74) *Attorney, Agent, or Firm* — Polsinelli PC

(57) ABSTRACT

Provided herein are compounds for the imaging and treatment of TDP43-mediated disorders. The compounds disclosed bind TDP43 aggregates and may be used to diagnose and treat amyotrophic lateral sclerosis (ALS) and frontotemporal dementia (FTD).

17 Claims, 7 Drawing Sheets
(2 of 7 Drawing Sheet(s) Filed in Color)

1

2

3

R₁ = H, Lower Alkyl (Me, Ethyl, etc); R₂ = H, X (Cl, F, Br, I);
X = F, Cl, Br, I

ORGANOMEDICINALS FOR IMAGING AND TREATMENT OF NEURODEGENERATIVE DISORDERS

CROSS REFERENCE TO RELATED APPLICATIONS

This application claims the benefit of U.S. provisional application No. 62/554,865, filed Sep. 6, 2017, the disclosures of which is hereby incorporated by reference in its entirety.

GOVERNMENTAL RIGHTS

This invention was made with government support under AG050263 awarded by the National Institute of Health. The government has certain rights in the invention.

FIELD OF THE INVENTION

Provided herein are compounds for the imaging and treatment of TDP43-mediated disorders. The compounds disclosed bind TDP43 aggregates and may be used to diagnose and treat amyotrophic lateral sclerosis (ALS) and frontotemporal dementia (FTD).

BACKGROUND

Frontotemporal lobar degeneration/frontotemporal dementia (FTLD/FTD) is the second most common form of non-Alzheimer's dementia worldwide in the population under 65 years, representing approximately 10-20% of all dementias[1] and normally appears with an average onset age group of mid to late 50s[2]. Clinically, frontotemporal dementia (FTD) is characterized by a progressive neuronal atrophy with loss in the frontal and temporal cortices, and is characterized by personality and behavioral changes, including gradual impairment of language skills. The disease can be distinguished in either familial or sporadic form and impacts equally men and women. As a familial form of disorder, it appears in ~40% of all FTLD cases[3]. In terms of its overlap with other neurodegenerative disorders, FTLD can appear alone or in combination with parkinsonism, progressive supranuclear palsy (PSP), corticobasal syndrome (CBS) and motor neuron disease (MND)[4-7]. Similarly, the characteristic features of ALS include, muscle loss (amyotrophic) due to the degeneration of lower motor neurons and their axons, including a loss of upper motor neurons and their corticospinal axonal tracts (lateral sclerosis). In general, ALS patients succumb to death between 3-5 years following onset of symptoms[8].

In terms of convergence of pathogenic mechanisms for diseases, while the largely indistinguishable, familial (10%) and sporadic (90%) ALS are characterized by premature degeneration of upper and lower motor neurons. Mutations in four genes (C9ORF72, SOD1, TARDBP, and FUS/TLS) account for over 50% of the familial ALS cases. For FTD, a stronger genetic contribution is noticeable with the higher percentage (up to 50%) of cases with a familial history. This includes the first two identified causal genes encoding the microtubule-associated protein tau (MAPT)[9] and progranulin (PGRN)[10,11], which together account for 10%-20% of FTD[12]. More rarely, mutations in TDP-43 and FUS/TLS are known to be causal for FTD[13]. Overall, it is commonly perceived that ALS and FTD are linked clinically, pathologically, and mechanistically, and thus both diseases are now properly recognized as representatives of a combination of broad neurodegenerative disorder, with each presenting in a spectrum of overlapping clinical symptoms. A recent breakthrough discovery has linked disease mechanisms for ALS and FTD by identifying TDP-43 as the major ubiquitinated protein found in both sporadic ALS patients and the most frequent pathological form of FTD[14,15.] Additionally, the role of TDP-43 in both sporadic and familial ALS was confirmed by the identification of mutations in the exon 6 of the TDP-43 encoding gene[16,17]. Furthermore, the pathogenesis of TDP-43 mutation in ALS has been validated in a variety of animal and cell models. Specifically, the overexpression of mutant TDP-43 has been shown to induce neuronal death in worms (Caenorhabditis elegans)[18], flies (Drosophila melanogaster)[19], zebrafish[20], mice[21], rats[22], monkeys[23], and cultured human motor neurons differentiated from reprogrammed stem cells[24].

TDP-43 is a 414 amino acid protein containing two RNA recognition motifs (RRMs) followed by a glycine-rich, low-sequence complexity prion-like domain. In terms of its normal functions, TDP-43 can act as a transcriptional repressor, and has been shown to be associated with proteins involved in transcription[25], including methyl CpG-binding protein 2 (MeCP2)[26], whose mutations are causative for Rett syndrome. Additionally, TDP-43 is involved in many aspects of RNA-related metabolism, including splicing, microRNA (miRNA) biogenesis, RNA transport and translation. TDP-43 has been demonstrated to shuttle between the cytosol and nucleus[27,28]. Although the majority of TDP-43 appears to be nuclear in most cells at a steady state. Pathological inclusions of TDP-43 has been found to be in the nucleus and cytosol of neurons and glia, with abnormal phosphorylation, ubiquitination of TDP-43 and the presence of truncated C-terminal fragments[14,15]. Approximately 40 mutations in sporadic and familial ALS, as well as in rare cases of FTD[29,30] have been found clustered primarily within the prion-like domain. Importantly, in the absence of mutations, TDP-43 pathology has been shown to be prevalent in the majority of ALS patients, with the exception of patients with SOD1 mutations[31,32], and is apparently indistinguishable between patients with or without TDP-43 mutations[33]. Typically, cells with TDP-43 aggregates have been shown to have a concomitant loss of nuclear TDP-43, thus implying loss of normal TDP-43 function. Importantly, the presence of cytoplasmic protein inclusions have been shown to induce neural toxicity. Overall, the pathogenic mechanisms for TDP-43 could result from a combination of both loss-of-its function and induction of toxicity. Combined aforementioned factors indicate that TDP-43 has emerged as a consistent and well-validated pathological biomarker for ALS/FTD. Therefore, the discovery, design, and development of a reliable, easily accessible, and highly sensitive yet specific PET/SPECT/OPTICAL probe for monitoring TDP-43 pathological inclusions would offer tremendous utility both in the diagnosis of ALS and/or FTD, while also enabling interrogation of efficacy for therapeutic drugs for treating these neurodegenerative disorders.

SUMMARY

One aspect of the present invention encompasses a compound comprising formula (I) or a pharmaceutically acceptable salt thereof:

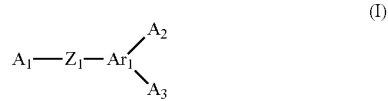

(I)

wherein:
Ar$_1$ is selected from the group consisting of:

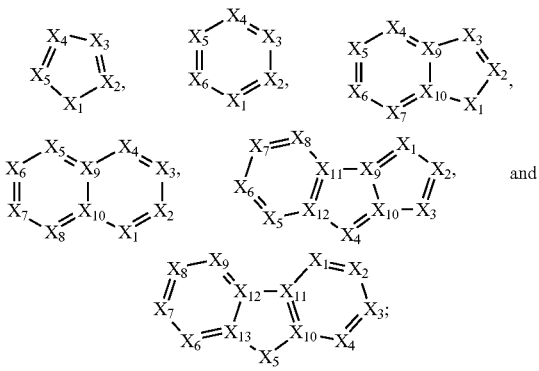

X$_1$-X$_{13}$ are independently selected from the group consisting of CH$_2$, CH, C, N, O, NR, S, and Se;
A$_1$-A$_3$ are independently selected from the group consisting of H, F, Cl, Br, I, CN, OH, NO$_2$, NHR, NRR$_1$, OR, SR, COOR, COR, amide, immino, sulfonic acid, 2-ethylidenemalononitrile, (E)-2-(but-2-en-1-ylidene)malononitrile, 2-((2E,4E)-hexa-2,4-dien-1-ylidene)malononitrile, acetyl, and —(OCH$_2$—CH$_2$)n$_3$,
wherein one or more A$_1$-A$_3$ optionally include a radionuclide;
R and R$_1$ are independently selected from the group consisting of H, a C$_1$-C$_{12}$ linear alkyl, alkene or alkyne, a C$_{1-12}$ branched chain alkyl, alkene, or alkyne, a C$_3$-C$_7$ cycloalkyl, a C$_1$-C$_{12}$ linear halo-alkyl, -alkene, or -alkyne, a C$_1$-C$_{12}$ branched chain halo-alkyl, -alkene, or -alkyne, or a combination thereof,
wherein one or both R and R$_1$ optionally include a radionuclide; and
Z$_1$ is selected from a C$_1$-C$_{12}$ linear or branched alkyl, ethylene glycol as single or multiple repeat units, COOR, COR, NHR,
wherein Z$_1$ is optionally conjugated to a chelator for chelation of a radionuclide or metal atom.

Another aspect of the invention encompasses a compound comprising formula (II) or a pharmaceutically acceptable salt thereof:

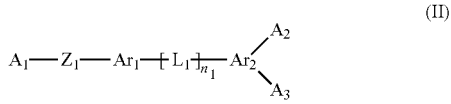
(II)

wherein:
Ar$_1$ and Ar$_2$ are independently selected from the group consisting of:

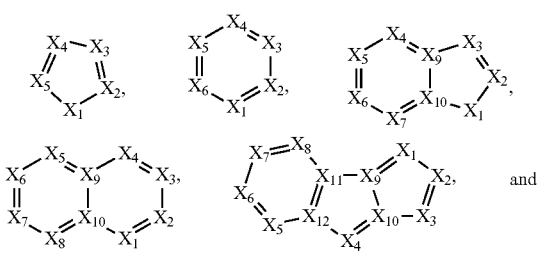

X$_1$-X$_{13}$ are independently selected from the group consisting of CH$_2$, CH, C, N, O, NR, S, and Se;
L$_1$ is selected from the group consisting of a C$_1$-C$_4$ alkyl, a C$_3$-C$_6$ cycloalkyl, isomers of straight or branched C$_2$-C$_8$ alkene, and a C$_1$-C$_8$ alkyne;
n$_1$ are integers from 0 to 3;
Z$_1$ is selected from the group consisting of CH$_2$, O, NR, S, and Se;
A$_1$-A$_3$ are independently selected from the group consisting of H, F, Cl, Br, I, CN, OH, NO$_2$, NHR, NRR$_1$, OR, SR, COOR, COR, amide, immino, sulfonic acid, 2-ethylidenemalononitrile, (E)-2-(but-2-en-1-ylidene)malononitrile, 2-((2E,4E)-hexa-2,4-dien-1-ylidene)malononitrile, acetyl, and —(OCH$_2$—CH$_2$)n$_3$,
wherein one or more A$_1$-A$_3$ optionally include a radionuclide;
R and R$_1$ are independently selected from the group consisting of H, a C$_1$-C$_{12}$ linear alkyl, alkene or alkyne, a C$_{1-12}$ branched chain alkyl, alkene, or alkyne, a C$_3$-C$_7$ cycloalkyl, a C$_1$-C$_{12}$ linear halo-alkyl, -alkene, or -alkyne, a C$_1$-C$_{12}$ branched chain halo-alkyl, -alkene, or -alkyne, or a combination thereof,
wherein one or both R and R$_1$ optionally include a radionuclide; and
Z$_1$ is selected from a C$_1$-C$_{12}$ linear or branched alkyl, ethylene glycol as single or multiple repeat units, COOR, COR, NHR,
wherein one or both of Z$_1$ is optionally conjugated to a chelator for chelation of a radionuclide or metal atom.

Another aspect of the invention encompasses a compound comprising formula (III) or a pharmaceutically acceptable salt thereof:

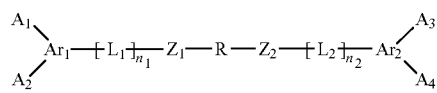
(III)

wherein:
Ar$_1$ and Ar$_2$ are independently selected from the group consisting of:

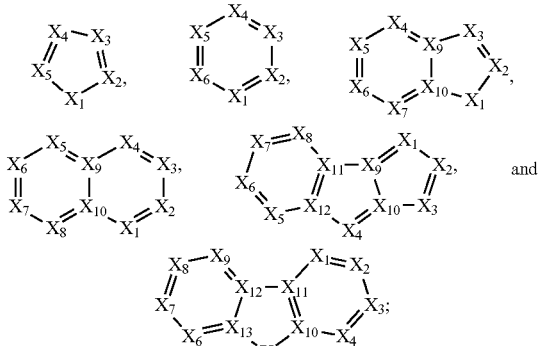

$X_1$-$X_{13}$ are independently selected from the group consisting of $CH_2$, CH, C, N, O, NR, S, and Se;

$L_1$ and $L_2$ are independently selected from the group consisting of a $C_1$-$C_4$ alkyl, a $C_3$-$C_6$ cycloalkyl, isomers of straight or branched $C_2$-$C_8$ alkene, and a $C_1$-$C_8$ alkyne;

$n_1$-$n_3$ are integers from 0 to 3;

$Z_1$ and $Z_2$ are independently selected from the group consisting of $CH_2$, O, NR, S, and Se;

$A_1$-$A_4$ are independently selected from the group consisting of H, F, Cl, Br, I, CN, OH, $NO_2$, NHR, $NRR_1$, OR, SR, COOR, COR, amide, immino, sulfonic acid, 2-ethylidenemalononitrile, (E)-2-(but-2-en-1-ylidene)malononitrile, 2-((2E,4E)-hexa-2,4-dien-1-ylidene)malononitrile, acetyl, and —$(OCH_2—CH_2)n_3$, wherein one or more $A_1$-$A_4$ optionally include a radionuclide;

R and $R_1$ are independently selected from the group consisting of H, a $C_1$-$C_{12}$ linear alkyl, alkene or alkyne, a $C_{1-12}$ branched chain alkyl, alkene, or alkyne, a $C_3$-$C_7$ cycloalkyl, a $C_1$-$C_{12}$ linear halo-alkyl, -alkene, or -alkyne, a $C_1$-$C_{12}$ branched chain halo-alkyl, -alkene, or -alkyne, or a combination thereof, wherein one or both R and $R_1$ optionally include a radionuclide; and $Z_1$ and $Z_2$ are independently selected from a $C_1$-$C_{12}$ linear or branched alkyl, ethylene glycol as single or multiple repeat units, COOR, COR, NHR, wherein one or both of $Z_1$ and $Z_2$ are optionally conjugated to a chelator for chelation of a radionuclide or metal atom.

In yet another aspect of the present invention encompasses a method for detecting, monitoring and/or treatment or prevention of a variety of TDP43-mediated disorders in a subject.

Still another aspect of the invention encompasses a method for detecting a variety of TDP43-mediated disorders in a subject. Non-limiting examples of TDP43-mediated disorders include frontotemporal dementia (FTD), amyotrophic lateral sclerosis (ALS), Alzheimer's disease, and glioblastoma multiforme (GBM).

Other aspects and iterations of the invention are described below.

BRIEF DESCRIPTION OF THE FIGURES

The application file contains at least one drawing executed in color. Copies of this patent application publication with color drawing(s) will be provided by the Office upon request and payment of the necessary fee.

DETAILED DESCRIPTION

Figure 1:
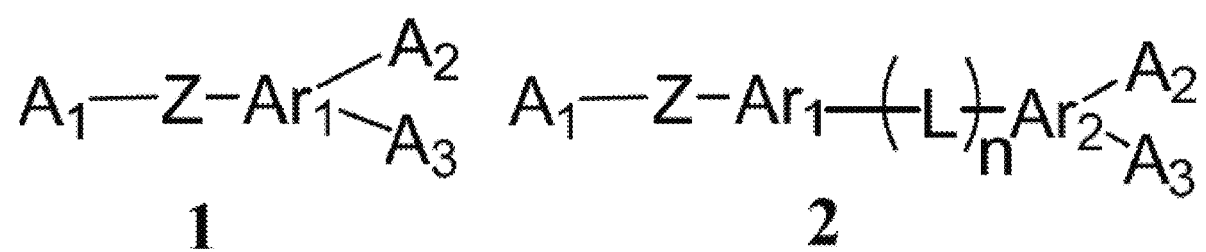
FIG. 1 depicts the general structure design of compounds of the disclosure, wherein $A_1$ represents a functional group or a substituent for incorporation of a radionuclide or any tracking motif, Z indicates a heteroatom (N, O, S etc), $Ar_1$ represents a single or a fused ring system, L represents a linker motif such as lower alkane, alkene, and alkyne, $Ar_2$ represents an aromatic single or fused ring system, $A_2$ and $A_3$ represent independently either a substituent within the ring or a functional group or linear or branched substituent comprising combination of C, H, N, O, S atoms or a combination thereof.

The present disclosure is directed to compounds that selectively bind aggregated TDP43. TDP43 is the major ubiquitinated protein found in both ALS and FTD. TDP43 is a 414 amino acid protein containing two RNA recognition motifs (RRMs) followed by a glycine-rich, low sequence complexity prion-like domain. Cells with TDP43 aggregates have been shown to have concomitant loss of nuclear TDP43, thus implying loss of normal TDP43 function. Importantly, the present of cytoplasmic protein inclusions have been shown to induce neural toxicity. Ultimately, TDP43 is a consistent and well-validated pathological biomarker for ALS and FTD. Accordingly, the compounds provided herein result in reliable, easily accessible, and highly sensitive yet specific imaging probes for monitoring TDP43 pathological inclusions. The compounds provided herein may be used to diagnosis ALS and/or FTD, while also enabling interrogation of efficacy for therapeutic drugs for treating these neurodegenerative diseases.

I. Compounds

In an aspect, the disclosure provides a compound or a pharmaceutically acceptable salt thereof of formula (I), (II), or (III):

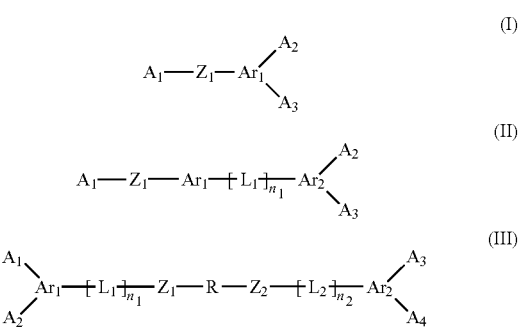

wherein:

$Ar_1$ and $Ar_2$ are independently selected from the group consisting of:

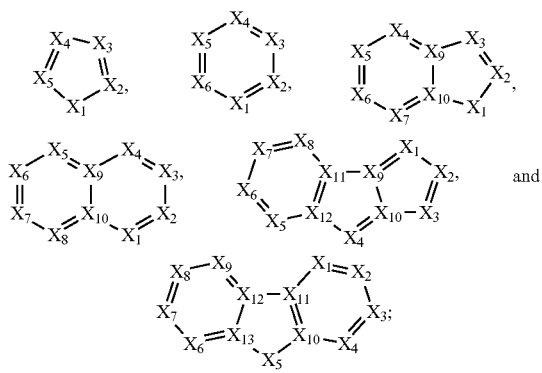

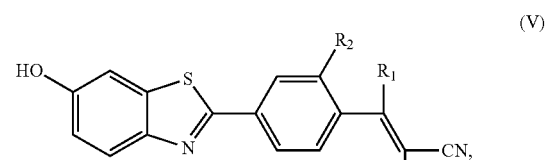

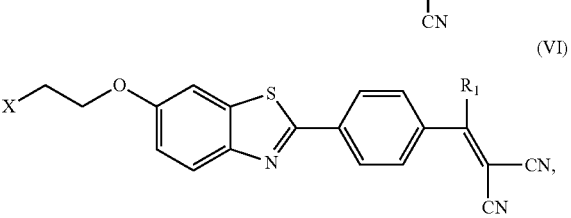

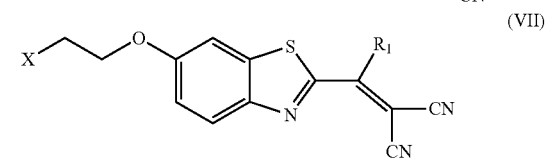

$X_1$-$X_{13}$ are independently selected from the group consisting of $CH_2$, CH, C, N, O, NR, S, and Se;

$L_1$ and $L_2$ are independently selected from the group consisting of a $C_1$-$C_4$ alkyl, a $C_3$-$C_6$ cycloalkyl, isomers of straight or branched $C_2$-$C_8$ alkene, and a $C_1$-$C_8$ alkyne;

$n_1$-$n_3$ are integers from 0 to 3;

$Z_1$ and $Z_2$ are independently selected from the group consisting of $CH_2$, O, NR, S, and Se;

$A_1$-$A_4$ are independently selected from the group consisting of H, F, Cl, Br, I, CN, OH, $NO_2$, NHR, $NRR_1$, OR, SR, COOR, COR, amide, immino, sulfonic acid, 2-ethylidenemalononitrile, (E)-2-(but-2-en-1-ylidene)malononitrile, 2-((2E,4E)-hexa-2,4-dien-1-ylidene)malononitrile, acetyl, and —($OCH_2$—$CH_2$)$n_3$, wherein one or more $A_1$-$A_4$ optionally include a radionuclide;

R and $R_1$ are independently selected from the group consisting of H, a $C_1$-$C_{12}$ linear alkyl, alkene or alkyne, a $C_{1-12}$ branched chain alkyl, alkene, or alkyne, a $C_3$-$C_7$ cycloalkyl, a $C_1$-$C_{12}$ linear halo-alkyl, -alkene, or -alkyne, a $C_1$-$C_{12}$ branched chain halo-alkyl, -alkene, or -alkyne, or a combination thereof, wherein one or both R and $R_1$ optionally include a radionuclide; and $Z_1$ and $Z_2$ are independently selected from a $C_1$-$C_{12}$ linear or branched alkyl, ethylene glycol as single or multiple repeat units, COOR, COR, NHR, wherein one or both of $Z_1$ and $Z_2$ are optionally conjugated to a chelator for chelation of a radionuclide or metal atom.

In certain embodiments, a compound of the disclosure is a compound of formula (IV):

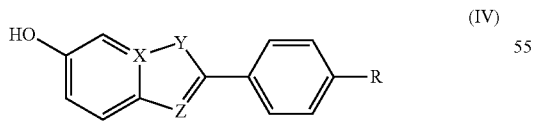

wherein:

X, Y, and Z are independently selected from the group consisting of C, N, O, and S; and R is selected from the group consisting of an alkyl chain or a functional group such as OH, CHO, COOH, COOR, amide, nitrile, $NO_2$, and a combination thereof.

In other embodiments, a compound of the disclosure is a compound of formula (V), (VI), or (VII):

wherein:

$R_1$ is selected from the group consisting of hydrogen and a $C_1$-$C_4$ alkyl;

$R_2$ is selected from the group consisting of hydrogen and a halogen; and

X is a halogen.

In still other embodiments, a compound of the disclosure is a compound of formula (VIII) or (IX):

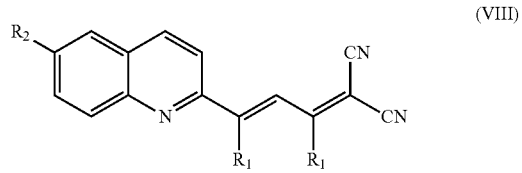

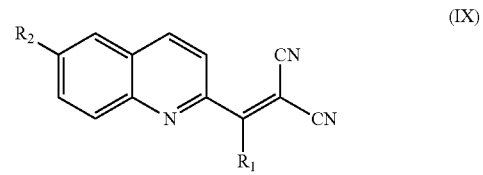

wherein:

$R_1$ is selected from the group consisting of hydrogen and a $C_1$-$C_4$ alkyl;

$R_2$ is selected from the group consisting of:

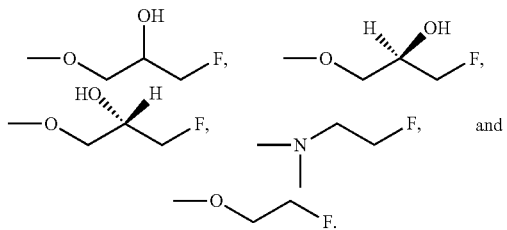

In each of the above emboiments, a radionuclide may be a γ-emitting radionuclide, Auger-emitting radionuclide, β-emitting radionuclide, an α-emitting radionuclide, or a positron-emitting radionuclide. A radionuclide may be a detectable label and/or a cytotoxic agent. Non-limiting examples of suitable radionuclides may include carbon-11, nitrogen-13, oxygen-15, fluorine-18, fluorodeoxyglucose-18, phosphorous-32, scandium-47, copper-64, 65 and 67, gallium-67 and 68, bromine-75, 76, 77 and 80m, rubidium-82, strontium-89, zirconium-89, yttrium-86 and 90, ruthenium-95, 97, 103 and 105, rhenium-99m, 101, 105, 186 and 188, technetium-99m, rhodium-105, mercury-107, palladium-109, indium-111, silver-111, indium-113m, lanthanide-114m, tin-117m, tellurium-121m, 122m and 125m, iodine-122, 123, 124, 125, 126, 131 and 133, praseodymium-142, promethium-149, samarium-153, gadolinium-159, thulium-165, 167 and 168, dysprosium-165, holmium-166, lutetium-177, rhenium-186 and 188, iridium-192, platinum-193 and 195m, gold-199, thallium-201, titanium-201, astatine-211, bismuth-212 and 213, lead-212, radium-223, actinium-225, and nitride or oxide forms derived therefrom. In a specific embodiment, a radionuclide is selected from the group consisting of carbon-11, fluorine-18, bromine-75, bromine-76, bromine-77, iodine-123, iodine-124, iodine-125, and iodine-131.

A variety of metal atoms may be included in a compound of the disclosure. The metal atom may generally be selected from the group of metal atoms comprised of metals with an atomic number of twenty or greater. For instance, the metal atoms may be calcium atoms, scandium atoms, titanium atoms, vanadium atoms, chromium atoms, manganese atoms, iron atoms, cobalt atoms, nickel atoms, copper atoms, zinc atoms, gallium atoms, germanium atoms, arsenic atoms, selenium atoms, bromine atoms, krypton atoms, rubidium atoms, strontium atoms, yttrium atoms, zirconium atoms, niobium atoms, molybdenum atoms, technetium atoms, ruthenium atoms, rhodium atoms, palladium atoms, silver atoms, cadmium atoms, indium atoms, tin atoms, antimony atoms, tellurium atoms, iodine atoms, xenon atoms, cesium atoms, barium atoms, lanthanum atoms, hafnium atoms, tantalum atoms, tungsten atoms, rhenium atoms, osmium atoms, iridium atoms, platinum atoms, gold atoms, mercury atoms, thallium atoms, lead atoms, bismuth atoms, francium atoms, radium atoms, actinium atoms, cerium atoms, praseodymium atoms, neodymium atoms, promethium atoms, samarium atoms, europium atoms, gadolinium atoms, terbium atoms, dysprosium atoms, holmium atoms, erbium atoms, thulium atoms, ytterbium atoms, lutetium atoms, thorium atoms, protactinium atoms, uranium atoms, neptunium atoms, plutonium atoms, americium atoms, curium atoms, berkelium atoms, californium atoms, einsteinium atoms, fermium atoms, mendelevium atoms, nobelium atoms, or lawrencium atoms. In some embodiments, the metal atoms may be selected from the group comprising alkali metals with an atomic number greater than twenty. In other embodiments, the metal atoms may be selected from the group comprising alkaline earth metals with an atomic number greater than twenty. In one embodiment, the metal atoms may be selected from the group of metals comprising the lanthanides. In another embodiment, the metal atoms may be selected from the group of metals comprising the actinides. In still another embodiment, the metal atoms may be selected from the group of metals comprising the transition metals. In yet another embodiment, the metal atoms may be selected from the group of metals comprising the poor metals. In other embodiments, the metal atoms may be selected from the group comprising gold atoms, bismuth atoms, tantalum atoms, and gadolinium atoms. In preferred embodiments, the metal atoms may be selected from the group comprising metals with an atomic number of 53 (i.e. iodine) to 83 (i.e. bismuth). In an alternative embodiment, the metal atoms may be atoms suitable for magnetic resonance imaging. In another alternative embodiment, the metal atoms may be selected from the group consisting of metals that have a K-edge in the x-ray energy band of CT. Preferred metal atoms include, but are not limited to, manganese, iron, gadolinium, gold, and iodine. In a specific embodiment, a metal atom is selected from the group consisting of gallium-67, gallium-68, unlabeled gallium, indium-111, iron-52, iron-59, copper-62, copper-64, thallium-201, technetium-99m, technetium-94m, rhenium-188, rubidium-82, strontium-92, yttrium-86, yttrium-90, zirconium-86, zirconium-89, a paramagnetic metal ion, and a lanthanide metal ion.

The metal atoms may be metal ions in the form of +1, +2, or +3 oxidation states. For instance, non-limiting examples include $Ba^{2+}$, $Bi^{3+}$, $Cs^+$, $Ca^{2+}$, $Cr^{2+}$, $Cr^{3+}$, $Cr^{6+}$, $Co^{2+}$, $Co^{3+}$, $Cu^+$, $Cu^{2+}$, $Cu^{3+}$, $Ga^{3+}$, $Gd^{3+}$, $Au^+$, $Au^{3+}$, $Fe^{2+}$, $Fe^{3+}$, $F^{3+}$, $Pb^{2+}$, $Mn^{2+}$, $Mn^{3+}$, $Mn^{4+}$, $Mn^{7+}$, $Hg^{2+}$, $Ni^{2+}$, $Ni^{3+}$, $Ag^+$, $Sr^{2+}$, $Sn^{2+}$, $Sn^{4+}$, and $Zn^{2+}$. The metal atoms may comprise a metal oxide. For instance, non-limiting examples of metal oxides may include iron oxide, manganese oxide, or gadolinium oxide. Additional examples may include magnetite, maghemite, or a combination thereof.

As used herein, a "chelator" or "chelating agent" is a molecule that forms multiple chemical bonds with a single metal atom. Prior to forming the bonds, the chelating agent has more than one pair of unshared electrons. The bonds are formed by sharing pairs of electrons with the metal atom. Examples of chelating agents include, but are not limited to, iminodicarboxylic and polyaminopolycarboxylic reactive groups, diethylenetriaminepentaacetic acid (DTPA), 1,4,7,10-tetraazacyclododecane-1,4,7,10-tetraacetic acid (DOTA), tetramethyl heptanedionate (TMHD), 2,4-pentanedione, ethylenediamine-tetraacetic acid disodium salt (EDTA), ethyleneglycol-O,O'-bis(2-aminoethyl)-N,N,N',N'-tetraacetic acid (EGTA), N-(2-hydroxyethyl)ethylenediamine-N,N',N'-triacetic acid trisodium salt (HEDTA), nitrilotriacetic acid (NTA), and 1,4,8,11-tetraazacyclotetradecane-N,N',N'',N'''-tetraacetic acid (TETA), deferoxamine (DFO), and derivatives thereof.

In an aspect, one or more atoms of a compound of the disclosure are replaced by a radioisotope. Non-limiting examples of atoms that can be replaced by a radioisotope include hydrogen, carbon, nitrogen, oxygen, sulfur and halogens such as bromine, fluorine, chlorine, and iodine. Non-limiting examples of radioisotopes include $^2H$, $^3H$, $^{11}C$, $^{13}C$, $^{14}C$, $^{15}N$, $^{18}O$, $^{35}S$, $^{75}Br$, $^{73}Br$, $^{77}Br$, $^{18}F$, $^{36}Cl$, $^{131}I$, $^{125}I$, $^{124}I$, and $^{123}I$.

In another aspect, a compound of the disclosure may be a prodrug. As used herein the term "prodrug" refers to a precursor of a designated compound that, following administration to a subject, yields the active ingredient in vivo induced by either a chemical or physiological process such as solvolysis or enzymatic cleavage under physiological conditions. Specifically, a prodrug within physiological pH is converted into an active species. A pharmaceutical acceptable prodrug is non-toxic, biologically tolerable, and suitable for administration to a subject.

In still another aspect, the compound of the disclosure may be converted into a pharmaceutically acceptable salt. "Pharmaceutically acceptable salts" are salts commonly used to form alkali metal salts and to form addition salts of free acids or free bases. The nature of the salt may vary, provided that it is pharmaceutically acceptable. Suitable pharmaceutically acceptable acid addition salts of compounds of the disclosure may be prepared from an inorganic acid or from an organic acid. Examples of such inorganic acids are hydrochloric, hydrobromic, hydroiodic, nitric, carbonic, sulfuric and phosphoric acid. Appropriate organic acids may be selected from aliphatic, cycloaliphatic, aromatic, araliphatic, heterocyclic, carboxylic and sulfonic classes of organic acids, examples of which are formic, acetic, propionic, succinic, glycolic, gluconic, lactic, malic, tartaric, citric, ascorbic, glucuronic, maleic, fumaric, pyruvic, aspartic, glutamic, benzoic, anthranilic, mesylic, 4-hydroxybenzoic, phenylacetic, mandelic, embonic (pamoic), methanesulfonic, ethanesulfonic, benzenesulfonic, pantothenic, 2-hydroxyethanesulfonic, toluenesulfonic, sulfanilic, cyclohexylaminosulfonic, stearic, algenic, hydroxybutyric, salicylic, galactaric and galacturonic acid. Suitable pharmaceutically acceptable base addition salts include metallic salts made from aluminum, calcium, lithium, magnesium, potassium, sodium and zinc or organic salts made from N,N'-dibenzylethylenediamine, chloroprocaine, choline, diethanolamine, ethylenediamine, meglumine-(N-methylglucamine) and procaine. All of these salts may be prepared by conventional means from the corresponding compound by reacting, for example, the appropriate acid or base with the any compound of the disclosure.

The compounds of the present disclosure have been shown to cross the blood-brain barrier (BBB). Accordingly, a compound of the disclosure may be conjugated to a therapeutic agent that would benefit from crossing the BBB. For example, a therapeutic agent used to treat a neurodegenerative disorder. Stated another way, a compound of the disclosure may be used to deliver a therapeutic agent across the BBB. In certain embodiment, a compound of the disclosure may be used to deliver an antioxidant across the BBB. For example, the antioxidant may be vitamin C.

(a) Nanoparticles

In an aspect, a compound of the disclosure is conjugated to or complexed with a nanoparticle. In certain embodiments, a nanoparticle is a magnetic nanoparticle. Magnetic nanoparticles as used and disclosed herein include those that are approved by FDA as MRI contrast enhancement agents. Magnetic nanoparticles are magnetic materials that have no dimension greater than 5 µm, such as less than 4 µm, less than 3 µm, less than 2 µm, less than 1 µm, less than 500 nm, less than 100 nm, or are about 2 to about 15 nm. Magnetic materials include iron, cobalt, zinc, cadmium, nickel, gadolinium, chromium, copper, manganese, terbium, europium, gold, silver, platinum, oxides of any of the preceding, alloys of any of the preceding, or mixtures thereof. Specific examples of magnetic materials include, but are not limited to, iron oxide, superparamagnetic iron oxide, $Fe_3O_4$, $Fe_2O_4$, $Fe_xPt_y$, $Co_xPt_y$, $MnFe_xO_y$, $CoFe_xO_y$, $NiFe_xO_y$, $CuFe_xO_y$, $ZnFe_xO_y$, and $CdFe_xO_y$, wherein x and y vary depending on the method of synthesis. In a specific embodiment, the nanoparticle is a gold nanoparticle. The gold may be Au-199 or Au-198.

A compound of the disclosure can be bound to the surface of the magnetic nanoparticles through a variety of means, including ionic interactions and covalent bonds. Ionic interactions between a compound of the disclosure and magnetic nanoparticles can occur between charged moieties or moieties capable of hydrogen bonding on the compound and the magnetic nanoparticle. Covalent bonds between the compound and the magnetic nanoparticle can be hydrolysable or releasable, such as ester bonds. For magnetic nanoparticles having hydroxyl groups on the surface, an ester bond can be formed between a compound having a carboxylic acid moiety and the magnetic nanoparticle.

In an aspect, a compound of the disclosure can be conjugated to a nanoparticle via a linker. A variety of linkers are suitable in the present disclosure, but typically the linker will impart a degree of flexibility to the compound of the disclosure. Generally speaking, the chain of atoms defining the linker can and will vary depending upon the embodiment. In an embodiment, a linker will comprise hydrocarbyl or substituted hydrocarbyl groups. In a typical alternative of this embodiment, the linker is from about 1 to about 50 atoms in length. Alternatively, the linker is from about 2 about 30 atoms in length. In an embodiment, the linker is from about 4 to about 20 atoms in length. The linker may comprise a variety of heteroatoms that may be saturated or unsaturated, substituted or unsubstituted, linear or cyclic, or straight or branched. The chain of atoms defining the linker will typically be selected from the group consisting of carbon, oxygen, nitrogen, sulfur, selenium, silicon and phosphorous. In an alternative embodiment, the chain of atoms is selected from the group consisting of carbon, oxygen, nitrogen, sulfur and selenium. In an embodiment, the linker will comprise substantially carbon and oxygen atoms. In addition, the chain of atoms defining the linker may be substituted or unsubstituted with atoms other than hydrogen, including, but not limited to, hydroxy, keto (=O), or acyl, such as acetyl. Thus, the chain may optionally include one or more ether, thioether, selenoether, amide, or amine linkages between hydrocarbyl or substituted hydrocarbyl regions. Exemplary linkers include ethylene glycol and aminohexanoic acid. More specifically, a linker may be a polyethylene glycol linker. Such a linker may be referred to as a heterobifunctional PEG linker or a homobifunctional PEG linker. In certain embodiments, a linker further comprises one or more spacers. Spacers are known in the art. Non-limiting examples of spacers include 2-aminoethoxy-2-ethoxy acetic acid (AEEA) linkers, AEEEA linkers, and AEA linkers. In an aspect, a linker is an aminothiol linker. See for example Abbas et al., *Langmuir* 2013; 29(1): 56-64, the disclosure of which is hereby incorporated by reference in its entirety. Specifically, the aminothiol linker may be an aminothiophenol linker. More specifically, the aminothiol linker may be a p-aminothiophenol linker.

In certain embodiments, the magnetic nanoparticles may have a hydroxyl functional group on their surface, which allows for ionic binding of a compound of the disclosure to the surface of the magnetic nanoparticle. This binding is reversible and allows for the bound compound to be released, such as at a target site. The amount of compound bound to the magnetic nanoparticle is controlled by the molar ratio of compound to magnetic nanoparticle, incubation time for mixing of the two components, the pH of the incubation, the temperature of the incubation, and/or the buffers used during the incubation. For example, it is known that phosphates interact strongly with iron oxide particles, and therefore, the presence of phosphates during incubation will impact the amount of compound bound to the magnetic nanoparticle surface. Binding of the compound to the magnetic nanoparticle provides a modified magnetic nanoparticle.

The magnetic nanoparticle optionally can have a coating over the magnetic material. Suitable coatings include dextran, chitosan, PLGA, dendrimers, amphiphilic polymers/bio-polymers (e.g. phospholipids and peptides), surfactants or chemical compounds with chelating properties for magnetic nanoparticles or high affinity adsorption (e.g. both chemisorption or physical adsorption) on the surface of magnetic nanoparticles, silicon oxide, silica, silica-PEG, mesoporous structures (silica or polymers or their combinations) for encapsulation of nanoparticles, or any other preferred combination of the above. In some cases, the coating is an amphiphilic polymer, for example, a phospholipid-PEG coating. Dextran-coated iron oxide nanoparticles have been approved for clinical human use by the FDA. Extensive studies on the biosafety, biodistribution, and metabolism of these superparamagnetic particles have shown that they are biocompatible and are degraded inside the body. The iron oxide is recycled and becomes raw materials for blood synthesis (hemoglobin).

The modified magnetic nanoparticles can be incorporated into liposomes. The liposomes can provide biocompatibility for the modified magnetic nanoparticles, allowing the therapeutic agent to be delivered passed the blood-brain barrier (BBB) by application of an external magnetic field. The liposomes can be formed by known means, such as by mixture of phosphatidyl choline, phosphatidyl ethanolamine, and cholesterol. The liposomes optionally can further be formed with dihexadecyl phosphate (DHDP) and distearoyl phosphatidyl ethanolamine (DSPE). The liposomes further can include polyethylene glycol moieties. For example, the liposome can be prepared using a phosphatidyl moiety further having a PEG moiety. The PEG moiety, if present, extends from the surface of the liposome into the surrounding environment. The presence of a PEG moiety stabilizes the circulating half life of the liposome and further can provide a sustained release type formulation for the compounds bound to the magnetic nanoparticles in the liposome.

(b) Components of the Composition

The present disclosure also provides pharmaceutical compositions. The pharmaceutical composition comprises a compound of the disclosure, as an active ingredient, and at least one pharmaceutically acceptable excipient.

The pharmaceutically acceptable excipient may be a diluent, a binder, a filler, a buffering agent, a pH modifying agent, a disintegrant, a dispersant, a preservative, a lubricant, taste-masking agent, a flavoring agent, or a coloring agent. The amount and types of excipients utilized to form pharmaceutical compositions may be selected according to known principles of pharmaceutical science.

In one embodiment, the excipient may be a diluent. The diluent may be compressible (i.e., plastically deformable) or abrasively brittle. Non-limiting examples of suitable compressible diluents include microcrystalline cellulose (MCC), cellulose derivatives, cellulose powder, cellulose esters (i.e., acetate and butyrate mixed esters), ethyl cellulose, methyl cellulose, hydroxypropyl cellulose, hydroxypropyl methylcellulose, sodium carboxymethylcellulose, corn starch, phosphated corn starch, pregelatinized corn starch, rice starch, potato starch, tapioca starch, starch-lactose, starch-calcium carbonate, sodium starch glycolate, glucose, fructose, lactose, lactose monohydrate, sucrose, xylose, lactitol, mannitol, malitol, sorbitol, xylitol, maltodextrin, and trehalose. Non-limiting examples of suitable abrasively brittle diluents include dibasic calcium phosphate (anhydrous or dihydrate), calcium phosphate tribasic, calcium carbonate, and magnesium carbonate.

In another embodiment, the excipient may be a binder. Suitable binders include, but are not limited to, starches, pregelatinized starches, gelatin, polyvinylpyrrolidone, cellulose, methylcellulose, sodium carboxymethylcellulose, ethylcellulose, polyacrylamides, polyvinyloxoazolidone, polyvinylalcohols, $C_{12}$-$C_{18}$ fatty acid alcohol, polyethylene glycol, polyols, saccharides, oligosaccharides, polypeptides, oligopeptides, and combinations thereof.

In another embodiment, the excipient may be a filler. Suitable fillers include, but are not limited to, carbohydrates, inorganic compounds, and polyvinylpyrrolidone. By way of non-limiting example, the filler may be calcium sulfate, both di- and tri-basic, starch, calcium carbonate, magnesium carbonate, microcrystalline cellulose, dibasic calcium phosphate, magnesium carbonate, magnesium oxide, calcium silicate, talc, modified starches, lactose, sucrose, mannitol, or sorbitol.

In still another embodiment, the excipient may be a buffering agent. Representative examples of suitable buffering agents include, but are not limited to, phosphates, carbonates, citrates, tris buffers, and buffered saline salts (e.g., Tris buffered saline or phosphate buffered saline).

In various embodiments, the excipient may be a pH modifier. By way of non-limiting example, the pH modifying agent may be sodium carbonate, sodium bicarbonate, sodium citrate, citric acid, or phosphoric acid.

In a further embodiment, the excipient may be a disintegrant. The disintegrant may be non-effervescent or effervescent. Suitable examples of non-effervescent disintegrants include, but are not limited to, starches such as corn starch, potato starch, pregelatinized and modified starches thereof, sweeteners, clays, such as bentonite, micro-crystalline cellulose, alginates, sodium starch glycolate, gums such as agar, guar, locust bean, karaya, pecitin, and tragacanth. Non-limiting examples of suitable effervescent disintegrants include sodium bicarbonate in combination with citric acid and sodium bicarbonate in combination with tartaric acid.

In yet another embodiment, the excipient may be a dispersant or dispersing enhancing agent. Suitable dispersants may include, but are not limited to, starch, alginic acid, polyvinylpyrrolidones, guar gum, kaolin, bentonite, purified wood cellulose, sodium starch glycolate, isoamorphous silicate, and microcrystalline cellulose.

In another alternate embodiment, the excipient may be a preservative. Non-limiting examples of suitable preservatives include antioxidants, such as BHA, BHT, vitamin A, vitamin C, vitamin E, or retinyl palmitate, citric acid, sodium citrate; chelators such as EDTA or EGTA; and antimicrobials, such as parabens, chlorobutanol, or phenol.

In a further embodiment, the excipient may be a lubricant. Non-limiting examples of suitable lubricants include minerals such as talc or silica; and fats such as vegetable stearin, magnesium stearate or stearic acid.

In yet another embodiment, the excipient may be a taste-masking agent. Taste-masking materials include cellulose ethers; polyethylene glycols; polyvinyl alcohol; polyvinyl alcohol and polyethylene glycol copolymers; monoglycerides or triglycerides; acrylic polymers; mixtures of acrylic polymers with cellulose ethers; cellulose acetate phthalate; and combinations thereof.

In an alternate embodiment, the excipient may be a flavoring agent. Flavoring agents may be chosen from synthetic flavor oils and flavoring aromatics and/or natural oils, extracts from plants, leaves, flowers, fruits, and combinations thereof.

In still a further embodiment, the excipient may be a coloring agent. Suitable color additives include, but are not limited to, food, drug and cosmetic colors (FD&C), drug and cosmetic colors (D&C), or external drug and cosmetic colors (Ext. D&C).

The weight fraction of the excipient or combination of excipients in the composition may be about 99% or less, about 97% or less, about 95% or less, about 90% or less, about 85% or less, about 80% or less, about 75% or less, about 70% or less, about 65% or less, about 60% or less, about 55% or less, about 50% or less, about 45% or less, about 40% or less, about 35% or less, about 30% or less, about 25% or less, about 20% or less, about 15% or less, about 10% or less, about 5% or less, about 2%, or about 1% or less of the total weight of the composition.

The composition can be formulated into various dosage forms and administered by a number of different means that will deliver a therapeutically effective amount of the active ingredient. Such compositions can be administered orally, parenterally, rectally, nasally, topically, ocularly, or by inhalation in dosage unit formulations containing conventional nontoxic pharmaceutically acceptable carriers, adjuvants, and vehicles as desired. Topical administration may also involve the use of transdermal administration such as transdermal patches or iontophoresis devices. The term parenteral as used herein includes subcutaneous, intravenous, intramuscular, or intrasternal injection, or infusion techniques. Formulation of drugs is discussed in, for example, Gennaro, A. R., Remington's Pharmaceutical Sciences, Mack Publishing Co., Easton, Pa. (18$^{th}$ ed, 1995), and Liberman, H. A. and Lachman, L., Eds., Pharmaceutical Dosage Forms, Marcel Dekker Inc., New York, N.Y. (1980).

Solid dosage forms for oral administration include capsules, tablets, caplets, pills, powders, pellets, and granules. In such solid dosage forms, the active ingredient is ordinarily combined with one or more pharmaceutically acceptable excipients, examples of which are detailed above. Oral preparations may also be administered as aqueous suspensions, elixirs, or syrups. For these, the active ingredient may be combined with various sweetening or flavoring agents, coloring agents, and, if so desired, emulsifying and/or suspending agents, as well as diluents such as water, ethanol, glycerin, and combinations thereof.

For parenteral administration (including subcutaneous, intradermal, intravenous, intramuscular, and intraperitoneal), the preparation may be an aqueous or an oil-based solution. Aqueous solutions may include a sterile diluent such as water, saline solution, a pharmaceutically acceptable polyol such as glycerol, propylene glycol, or other synthetic solvents; an antibacterial and/or antifungal agent such as benzyl alcohol, methyl paraben, chlorobutanol, phenol, thimerosal, and the like; an antioxidant such as ascorbic acid or sodium bisulfite; a chelating agent such as etheylenediaminetetraacetic acid; a buffer such as acetate, citrate, or phosphate; and/or an agent for the adjustment of tonicity such as sodium chloride, dextrose, or a polyalcohol such as mannitol or sorbitol. The pH of the aqueous solution may be adjusted with acids or bases such as hydrochloric acid or sodium hydroxide. Oil-based solutions or suspensions may further comprise sesame, peanut, olive oil, or mineral oil.

The compositions may be presented in unit-dose or multi-dose containers, for example sealed ampoules and vials, and may be stored in a freeze-dried (lyophilized) condition requiring only the addition of the sterile liquid carried, for example water for injections, immediately prior to use. Extemporaneous injection solutions and suspensions may be prepared from sterile powders, granules and tablets.

For topical (e.g., transdermal or transmucosal) administration, penetrants appropriate to the barrier to be permeated are generally included in the preparation. Pharmaceutical compositions adapted for topical administration may be formulated as ointments, creams, suspensions, lotions, powders, solutions, pastes, gels, sprays, aerosols or oils. In some embodiments, the pharmaceutical composition is applied as a topical ointment or cream. When formulated in an ointment, the active ingredient may be employed with either a paraffinic or a water-miscible ointment base. Alternatively, the active ingredient may be formulated in a cream with an oil-in-water cream base or a water-in-oil base. Pharmaceutical compositions adapted for topical administration to the eye include eye drops wherein the active ingredient is dissolved or suspended in a suitable carrier, especially an aqueous solvent. Pharmaceutical compositions adapted for topical administration in the mouth include lozenges, pastilles and mouth washes. Transmucosal administration may be accomplished through the use of nasal sprays, aerosol sprays, tablets, or suppositories, and transdermal administration may be via ointments, salves, gels, patches, or creams as generally known in the art.

In certain embodiments, a composition comprising a compound of the disclosure is encapsulated in a suitable vehicle to either aid in the delivery of the compound to target cells, to increase the stability of the composition, or to minimize potential toxicity of the composition. As will be appreciated by a skilled artisan, a variety of vehicles are suitable for delivering a composition of the present invention. Non-limiting examples of suitable structured fluid delivery systems may include nanoparticles, liposomes, microemulsions, micelles, dendrimers and other phospholipid-containing systems. Methods of incorporating compositions into delivery vehicles are known in the art.

In one alternative embodiment, a liposome delivery vehicle may be utilized. Liposomes, depending upon the embodiment, are suitable for delivery of a compound of the disclosure in view of their structural and chemical properties. Generally speaking, liposomes are spherical vesicles with a phospholipid bilayer membrane. The lipid bilayer of a liposome may fuse with other bilayers (e.g., the cell membrane), thus delivering the contents of the liposome to cells. In this manner, a compound of the disclosure may be selectively delivered to a cell by encapsulation in a liposome that fuses with the targeted cell's membrane.

Liposomes may be comprised of a variety of different types of phosolipids having varying hydrocarbon chain lengths. Phospholipids generally comprise two fatty acids linked through glycerol phosphate to one of a variety of polar groups. Suitable phospholids include phosphatidic acid (PA), phosphatidylserine (PS), phosphatidylinositol (PI), phosphatidylglycerol (PG), diphosphatidylglycerol (DPG), phosphatidylcholine (PC), and phosphatidylethanolamine (PE). The fatty acid chains comprising the phospholipids may range from about 6 to about 26 carbon atoms in length, and the lipid chains may be saturated or unsaturated. Suitable fatty acid chains include (common name presented in parentheses) n-dodecanoate (laurate), n-tretradecanoate (myristate), n-hexadecanoate (palmitate), n-octadecanoate (stearate), n-eicosanoate (arachidate), n-docosanoate (behenate), n-tetracosanoate (lignocerate), cis-9-hexadecenoate (palmitoleate), cis-9-octadecanoate (oleate), cis,cis-9,12-octadecandienoate (linoleate), all cis-9, 12, 15-octadecatrienoate (linolenate), and all cis-5,8,11,14-eicosatetraenoate (arachidonate). The two fatty acid chains of a phospholipid may be identical or different. Acceptable phospholipids include dioleoyl PS, dioleoyl PC, distearoyl PS, distearoyl PC, dimyristoyl PS, dimyristoyl PC, dipalmitoyl PG, stearoyl, oleoyl PS, palmitoyl, linolenyl PS, and the like.

The phospholipids may come from any natural source, and, as such, may comprise a mixture of phospholipids. For example, egg yolk is rich in PC, PG, and PE, soy beans contains PC, PE, PI, and PA, and animal brain or spinal cord is enriched in PS. Phospholipids may come from synthetic sources too. Mixtures of phospholipids having a varied ratio of individual phospholipids may be used. Mixtures of different phospholipids may result in liposome compositions having advantageous activity or stability of activity properties. The above mentioned phospholipids may be mixed, in optimal ratios with cationic lipids, such as N-(1-(2,3-dioleolyoxy)propyl)-N,N,N-trimethyl ammonium chloride, 1,1'-dioctadecyl-3,3,3',3'-tetramethylindocarbocyanine perchloarate, 3,3'-deheptyloxacarbocyanine iodide, 1,1'-dedodecyl-3,3,3',3'-tetramethylindocarbocyanine perchloarate, 1,1'-dioleyl-3,3,3',3'-tetramethylindo carbocyanine methanesulfonate, N-4-(delinoleylaminostyryl)-N-methylpyridinium iodide, or 1,1,-dilinoleyl-3,3,3',3'-tetramethylindocarbocyanine perchloarate.

Liposomes may optionally comprise sphingolipids, in which spingosine is the structural counterpart of glycerol and one of the one fatty acids of a phosphoglyceride, or cholesterol, a major component of animal cell membranes. Liposomes may optionally contain pegylated lipids, which are lipids covalently linked to polymers of polyethylene glycol (PEG). PEGs may range in size from about 500 to about 10,000 daltons.

Liposomes may further comprise a suitable solvent. The solvent may be an organic solvent or an inorganic solvent. Suitable solvents include, but are not limited to, dimethylsulfoxide (DMSO), methylpyrrolidone, N-methylpyrrolidone, acetronitrile, alcohols, dimethylformamide, tetrahydrofuran, or combinations thereof.

Liposomes carrying a compound of the disclosure (i.e., having at least one methionine compound) may be prepared by any known method of preparing liposomes for drug delivery, such as, for example, detailed in U.S. Pat. Nos. 4,241,046, 4,394,448, 4,529,561, 4,755,388, 4,828,837, 4,925,661, 4,954,345, 4,957,735, 5,043,164, 5,064,655, 5,077,211 and 5,264,618, the disclosures of which are hereby incorporated by reference in their entirety. For example, liposomes may be prepared by sonicating lipids in an aqueous solution, solvent injection, lipid hydration, reverse evaporation, or freeze drying by repeated freezing and thawing. In a preferred embodiment the liposomes are formed by sonication. The liposomes may be multilamellar, which have many layers like an onion, or unilamellar. The liposomes may be large or small. Continued high-shear sonication tends to form smaller unilamellar lipsomes.

As would be apparent to one of ordinary skill, all of the parameters that govern liposome formation may be varied. These parameters include, but are not limited to, temperature, pH, concentration of methionine compound, concentration and composition of lipid, concentration of multivalent cations, rate of mixing, presence of and concentration of solvent.

In another embodiment, a composition of the invention may be delivered to a cell as a microemulsion. Microemulsions are generally clear, thermodynamically stable solutions comprising an aqueous solution, a surfactant, and "oil." The "oil" in this case, is the supercritical fluid phase. The surfactant rests at the oil-water interface. Any of a variety of surfactants are suitable for use in microemulsion formulations including those described herein or otherwise known in the art. The aqueous microdomains suitable for use in the invention generally will have characteristic structural dimensions from about 5 nm to about 100 nm. Aggregates of this size are poor scatterers of visible light and hence, these solutions are optically clear. As will be appreciated by a skilled artisan, microemulsions can and will have a multitude of different microscopic structures including sphere, rod, or disc shaped aggregates. In one embodiment, the structure may be micelles, which are the simplest microemulsion structures that are generally spherical or cylindrical objects. Micelles are like drops of oil in water, and reverse micelles are like drops of water in oil. In an alternative embodiment, the microemulsion structure is the lamellae. It comprises consecutive layers of water and oil separated by layers of surfactant. The "oil" of microemulsions optimally comprises phospholipids. Any of the phospholipids detailed above for liposomes are suitable for embodiments directed to microemulsions. A compound of the disclosure may be encapsulated in a microemulsion by any method generally known in the art.

In yet another embodiment, a compound of the disclosure may be delivered in a dendritic macromolecule, or a dendrimer. Generally speaking, a dendrimer is a branched tree-like molecule, in which each branch is an interlinked chain of molecules that divides into two new branches (molecules) after a certain length. This branching continues until the branches (molecules) become so densely packed that the canopy forms a globe. Generally, the properties of dendrimers are determined by the functional groups at their surface. For example, hydrophilic end groups, such as carboxyl groups, would typically make a water-soluble dendrimer. Alternatively, phospholipids may be incorporated in the surface of a dendrimer to facilitate absorption across the skin. Any of the phospholipids detailed for use in liposome embodiments are suitable for use in dendrimer embodiments. Any method generally known in the art may be utilized to make dendrimers and to encapsulate compositions of the invention therein. For example, dendrimers may be produced by an iterative sequence of reaction steps, in which each additional iteration leads to a higher order dendrimer. Consequently, they have a regular, highly branched 3D structure, with nearly uniform size and shape. Furthermore, the final size of a dendrimer is typically controlled by the number of iterative steps used during synthesis. A variety of dendrimer sizes are suitable for use in the invention. Generally, the size of dendrimers may range from about 1 nm to about 100 nm.

II. Methods

A compound of the disclosure may be used for metabolic studies, reactions kinetics, pharmacokinetic studies, pharmacodynamics studies, and/or diagnostic nuclear medicine (e.g. PET and SPECT imaging). Accordingly, the present disclosure encompasses a method for detecting, monitoring and/or treatment or prevention of a variety of TDP43-mediated disorders in a subject. Specifically, the present invention encompasses a method for detecting a variety of TDP43-mediated disorders in a subject. Non-limiting examples of TDP43-mediated disorders include frontotemporal dementia (FTD), amyotrophic lateral sclerosis (ALS), Alzheimer's disease, and glioblastoma multiforme (GBM).

In an aspect, the present disclosure encompasses a method for detecting TDP43 aggregates in a sample. The method comprises contacting a sample with a compound of the disclosure and detecting the presence of a signal emitted from the compound of the disclosure, the signal being emitted from binding of the compound to one or more TDP43 aggregates in the sample. The sample may be a biological sample obtained from a subject. Binding may be detected using microscopy (fluorescent microscopy, confocal microscopy, or electron microscopy), magnetic resonance imaging (including MTI, MRS, DWI and fMRI), scintigraphic imaging (SPECT (Single Photon Emission Computed Tomography), PET (Positron Emission Tomography), gamma camera imaging, and rectilinear scanning), radiography, or ultrasound. The compound may be detectable in situ, in vivo, ex vivo, and in vitro.

In another aspect, the present disclosure encompasses a method for detecting TDP43 aggregates in a subject. The method comprises administering to a subject a composition comprising a compound of the disclosure and detecting the presence of a signal emitted from the compound of the disclosure, the signal being emitted from binding of the compound to one or more TDP43 aggregates in the subject.

In still another aspect, the present disclosure encompasses a method for preventing or inhibiting TDP43 aggregation in a sample or a subject. The method comprises contacting a sample or administering to a subject a compound of the disclosure, wherein the compound binds TDP43 aggregates. In certain embodiments, at least one of $Z_1$, $Z_2$, $X_2$ and $X_3$ of a compound of the disclosure is Se or S.

In still yet another aspect, the present disclosure encompasses a method for detecting, monitoring and/or treatment or prevention of TDP43-mediated disorders. The method comprises administering an effective amount of a composition comprising a compound of the disclosure to a subject; and detecting the presence of a signal emitted from the compound of the disclosure in the subject, wherein detection of signal above baseline indicates a TDP43-mediated disorder. In a specific embodiment, the present invention encompasses a method for detecting a TDP43-mediated disorder in a subject. In certain embodiments, the method may measure the distribution of TDP43 aggregates in a subject. The term "treat", "treating" or "treatment" as used herein refers to administering a compound of the disclosure for prophylactic and/or therapeutic purposes. The term "prophylactic treatment" refers to treating a subject who is not yet experiencing symptoms, but who may have, or otherwise at a risk of having a TDP43-mediated disorder. The term "therapeutic treatment" refers to administering treatment to a subject already suffering from a TDP43-mediated disorder. The term "treat", "treating" or "treatment" as used herein also refers to administering a compound of the disclosure in order to: (i) reduce or eliminate either TDP43-aggregates or one or more symptoms of the TDP43-mediated disorder, or (ii) retard the progression of a TDP43-mediated disorder or of one or more symptoms of the TDP43-mediated disorder, or (iii) reduce the severity of a TDP43-mediated disorder or of one or more symptoms of the TDP43-mediated disorder, or (iv) suppress the clinical manifestation of a TDP43-mediated disorder, or (v) suppress the manifestation of adverse symptoms of the TDP43-mediated disorder.

In a different aspect, the present disclosure encompasses a method for detecting TDP43-mediated tumorigenicity of glioblastoma cells in malignant brain tumors. The method comprising administering an effective amount of a composition comprising a compound of the disclosure to a subject; and detecting the presence of a signal emitted from the compound in the subject, wherein detection of signal above baseline indicates TDP43-mediated tumorigenicity of glioblastoma cells. Detection of TDP43-mediated GBM can inform treatment decisions for GBM.

The disclosure comprises, in part, imaging a subject. Non-limiting examples of modalities of imaging may include magnetic resonance imaging (MRI), ultrasound (US), computed tomography (CT), Positron Emission Tomography (PET), Single Photon Emission Computed Tomography (SPECT), and optical imaging (OI, bioluminescence and fluorescence). Radioactive molecular probes are traditionally imaged with PET, SPECT or gamma (γ) cameras, by taking advantage of the capability of these imaging modalities to detect the high energetic γ rays. In contrast, OI generally detects low energy lights (visible or near-infrared lights) emitted from bioluminescence or fluorescence probes.

Suitable subjects include, but are not limited to, a human, a livestock animal, a companion animal, a lab animal, and a zoological animal. A subject may or may not be known to have a TDP43-mediated disorder. In one embodiment, the subject may be a rodent, e.g. a mouse, a rat, a guinea pig, etc. In another embodiment, the subject may be a livestock animal. Non-limiting examples of suitable livestock animals may include pigs, cows, horses, goats, sheep, llamas and alpacas. In yet another embodiment, the subject may be a companion animal. Non-limiting examples of companion animals may include pets such as dogs, cats, rabbits, and birds. In yet another embodiment, the subject may be a zoological animal. As used herein, a "zoological animal" refers to an animal that may be found in a zoo. Such animals may include non-human primates, large cats, wolves, and bears. In a preferred embodiment, the animal is a laboratory animal. Non-limiting examples of a laboratory animal may include rodents, canines, felines, and non-human primates. In another preferred embodiment, the subject is a human.

As used herein, "baseline" may be the background signal. Alternatively, baseline may be no signal. In a specific embodiment, baseline is the signal detected in uninvolved tissue. A skilled artisan would be able to determine the baseline of a signal. By above is meant that the signal is greater than the baseline signal. For example, the signal may be at least 2% greater than baseline. For example, the signal may be at least 2%, at least 5%, at least 10%, at least 20%, at least 30%, at least 40%, at least 50%, at least 60%, at least 70%, at least 80%, at least 90%, or at least 100% greater than baseline. In a specific embodiment, the signal is >20% above baseline. In other embodiments, the signal may be increased at least 2-fold over baseline. For example, the signal may be increased at least 2-fold, at least 5-fold, at least 10-fold, at least 15-fold, at least 20-fold, at least 25-fold, at least 30-fold, at least 35-fold, at least 40-fold, at least 45-fold, or at least 50-fold over baseline.

The term "signal" as used herein, refers to a signal derived from a compound that can be detected and quantitated with regards to its frequency and/or amplitude. The signal can be generated from one or more compounds of the present disclosure. In an embodiment, the signal may need to be the sum of each of the individual signals. In an embodiment, the signal can be generated from a summation, an integration, or other mathematical process, formula, or algorithm, where the signal is from one or more compounds. In an embodiment, the summation, the integration, or other mathematical process, formula, or algorithm can be used to generate the signal so that the signal can be distinguished from background noise and the like. It should be noted that signals other than the signal of interest can be processed and/or obtained in a similar manner as that of the signal of interest.

Using a method of the disclosure, microscopic lesions of TDP43 aggregates may be detected in a subject. Such lesions are generally not visible with current imaging techniques. Further the compounds of the disclosure may be used to improve early diagnosis and interrogate the efficacy of therapeutics for the treatment of TDP43-mediated disorders.

In certain aspects, a pharmacologically effective amount of a compound of the disclosure may be administered to a subject. Administration is performed using standard effective techniques, including peripherally (i.e. not by administration into the central nervous system) or locally to the central nervous system. Peripheral administration includes but is not limited to intravenous, intraperitoneal, subcutaneous, pulmonary, transdermal, intramuscular, intranasal, buccal, sublingual, or suppository administration. Local administration, including directly into the central nervous system (CNS) includes but is not limited to via a lumbar, intraventricular or intraparenchymal catheter or using a surgically implanted controlled release formulation.

Pharmaceutical compositions for effective administration are deliberately designed to be appropriate for the selected mode of administration, and pharmaceutically acceptable excipients such as compatible dispersing agents, buffers, surfactants, preservatives, solubilizing agents, isotonicity agents, stabilizing agents and the like are used as appropriate. Remington's Pharmaceutical Sciences, Mack Publishing Co., Easton Pa., 16Ed ISBN: 0-912734-04-3, latest edition, incorporated herein by reference in its entirety, provides a compendium of formulation techniques as are generally known to practitioners. It may be particularly useful to alter the solubility characteristics of the compounds useful in this discovery, making them more lipophilic, for example, by encapsulating them in liposomes or by blocking polar groups.

Effective peripheral systemic delivery by intravenous or intraperitoneal or subcutaneous injection is a preferred method of administration to a living patient. Suitable vehicles for such injections are straightforward. In addition, however, administration may also be effected through the mucosal membranes by means of nasal aerosols or suppositories. Suitable formulations for such modes of administration are well known and typically include surfactants that facilitate cross-membrane transfer. Such surfactants are often derived from steroids or are cationic lipids, such as N-[1-(2,3-dioleoyl)propyl]-N,N,N-trimethyl ammonium chloride (DOTMA) or various compounds such as cholesterol hemisuccinate, phosphatidyl glycerols and the like.

For therapeutic applications, a therapeutically effective amount of a compound of the disclosure is administered to a subject. A "therapeutically effective amount" is an amount of the therapeutic composition sufficient to produce a measurable biological response (e.g., reduction in TDP43 aggregates, reduction in symptoms associated with TDP43-mediated disorders). Actual dosage levels of active ingredients in a therapeutic composition of the disclosure can be varied so as to administer an amount of the active compound(s) that is effective to achieve the desired therapeutic response for a particular subject. The selected dosage level will depend upon a variety of factors including the activity of the therapeutic composition, formulation, the route of administration, combination with other drugs or treatments, TDP43 aggregate size and longevity, and the physical condition and prior medical history of the subject being treated. In some embodiments, a minimal dose is administered, and dose is escalated in the absence of dose-limiting toxicity. Determination and adjustment of a therapeutically effective dose, as well as evaluation of when and how to make such adjustments, are known to those of ordinary skill in the art of medicine.

For diagnostic applications, a detectable amount of a compound of the disclosure is administered to a subject. A "detectable amount", as used herein to refer to a diagnostic composition, refers to a dose of such a compound that the presence of the compound can be determined in vivo or in vitro. A detectable amount will vary according to a variety of factors, including but not limited to chemical features of the compound, labeling methods, the method of imaging and parameters related thereto, metabolism of the compound in the subject, the stability of the compound (e.g. the half-life of a radionuclide label), the time elapsed following administration of the compound prior to imaging, the route of drug administration, the physical condition and prior medical history of the subject, and the size and longevity of the TDP43 aggregate or suspected TDP43 aggregate. Thus, a detectable amount can vary and can be tailored to a particular application. After study of the present disclosure, and in particular the Examples, it is within the skill of one in the art to determine such a detectable amount. A detectable amount may be visible from about 1 to about 120 hours or more. For example, a detectable amount may be visible from about 1 to about 110 hours, or from about 1 to about 100 hours. Accordingly, a detectable amount may be visible at about 1, about 2, about 3, about 4, about 5, about 6, about 7, about 8, about 9, about 10, about 11, about 12, about 16, about 24, about 36, about 48, about 60, about 72, about 84, about 96, about 108, or about 120 hours.

The frequency of dosing may be daily or once, twice, three times or more per week or per month, as needed as to effectively treat the symptoms. The timing of administration of the treatment relative to the disease itself and duration of treatment will be determined by the circumstances surrounding the case. Treatment could begin immediately. Treatment could begin in a hospital or clinic itself, or at a later time after discharge from the hospital or after being seen in an outpatient clinic. Duration of treatment could range from a single dose administered on a one-time basis to a life-long course of therapeutic treatments.

Although the foregoing methods appear the most convenient and most appropriate and effective for administration of peptide constructs, by suitable adaptation, other effective techniques for administration, such as intraventricular administration, transdermal administration and oral administration may be employed provided proper formulation is utilized herein.

In addition, it may be desirable to employ controlled release formulations using biodegradable films and matrices, or osmotic mini-pumps, or delivery systems based on dextran beads, alginate, or collagen.

Typical dosage levels can be determined and optimized using standard clinical techniques and will be dependent on the mode of administration.

In certain aspects, the method of the disclosure may further comprise detection of additional genes or proteins for the detection or diagnosis of neurodegenerative disorders. Non-limiting examples of additional genes that may be detected include C9ORF72, SOD1, TARDBP, FUS/TLS, MAPT, and PGRN. Non-limiting example of additional proteins that may be detected include ubiquitin, tau, and α-synuclein.

In certain aspects, the methods of the invention may further comprise administering therapeutic agents standard for the treatment of TDP43-mediated disorders. Suitable therapeutic agents for TDP43-mediated disorders are known in the art, and will depend upon the type and stage of TDP43-mediated disorder. Non-limiting examples of therapeutic agents for TDP43-mediated disorders include vitamin C, rapamycin, CDK, c-JNK inhibitors, and triptolide.

DEFINITIONS

The term "hydrocarbyl" as used herein describe organic compounds or radicals consisting exclusively of the elements carbon and hydrogen. These moieties include alkyl, alkenyl, alkynyl, and aryl moieties. These moieties also include alkyl, alkenyl, alkynyl, and aryl moieties substituted with other aliphatic or cyclic hydrocarbon groups, such as alkaryl, alkenaryl and alkynaryl. Unless otherwise indicated, these moieties preferably comprise 1 to 20 carbon atoms.

The term "substituted hydrocarbyl" moieties described herein are hydrocarbyl moieties which are substituted with at least one atom other than carbon, including moieties in which a carbon chain atom is substituted with a hetero atom such as nitrogen, oxygen, silicon, phosphorous, boron, sulfur, or a halogen atom. These substituents include halogen, carbocycle, aryl, heterocyclo, alkoxy, alkenoxy, alkynoxy, aryloxy, hydroxy, protected hydroxy, keto, acyl, acyloxy, nitro, amino, amido, nitro, cyano, thiol, ketals, acetals, esters and ethers.

EXAMPLES

The following examples are included to demonstrate various embodiments of the present disclosure. It should be appreciated by those of skill in the art that the techniques disclosed in the examples that follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Figure 2:
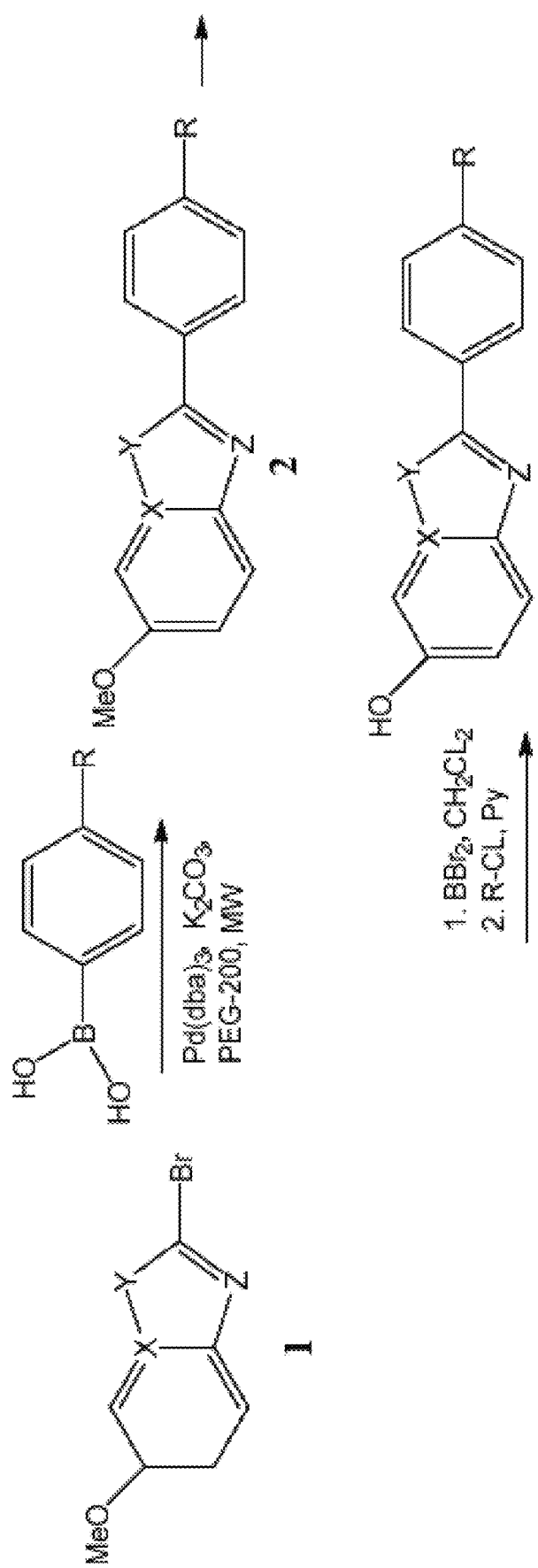
FIG. 2 depicts a scheme showing synthesis of small organic molecules (including SHAR165); wherein X, Y, Z represent independently of C, N, O, S, and R represents either alkyl chain or a functional group, such as OH, CHO, COOH, COOR, Amide, Nitrile, $NO_2$, etc or a combination thereof.

Based upon our observation of literature precedents that C-terminal fragments of human TDP-43 are frequently detected in tissue samples of ALS patients[15,34,35], we have designed and discovered a class of small organic molecules with a general structure (FIG. 1) using molecular dynamics targeted to a domain within the C-terminus fragments. To accomplish chemical synthesis, representative example of heterocyclic small organic molecules were synthesized (using scheme shown FIG. 2), purified either via flash chromatography or HPLC and analytically characterized using NMR (Proton and $^{13}$C-NMR) and LCMS.

Figure 3:
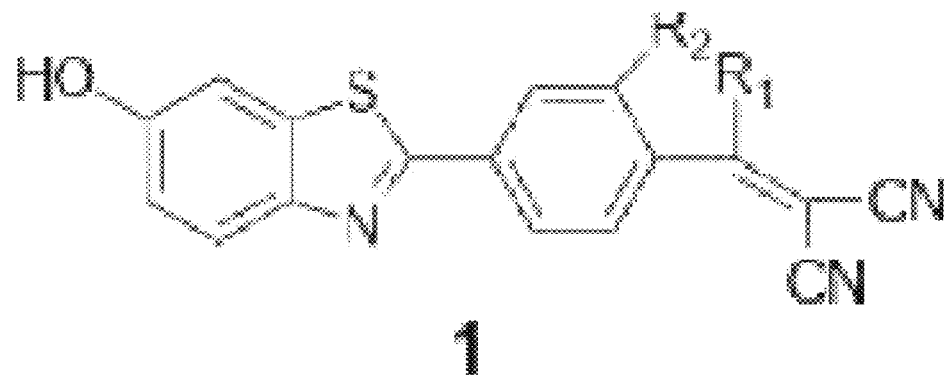
FIG. 3 depicts derivatives 1, 2 and 3.
Figure 3:
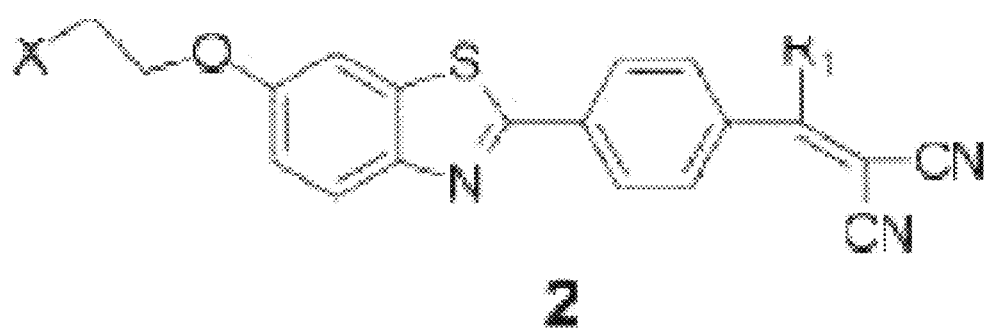
Figure 3:
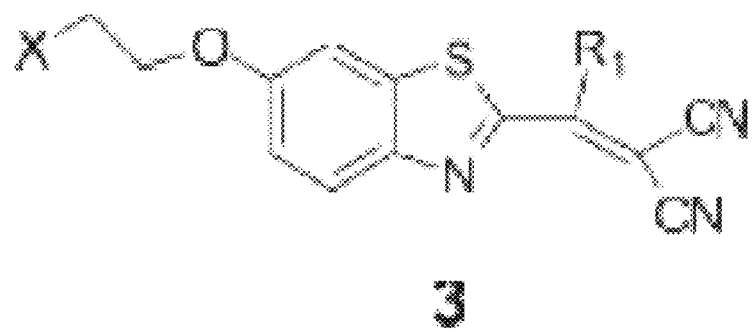
Figure 4:
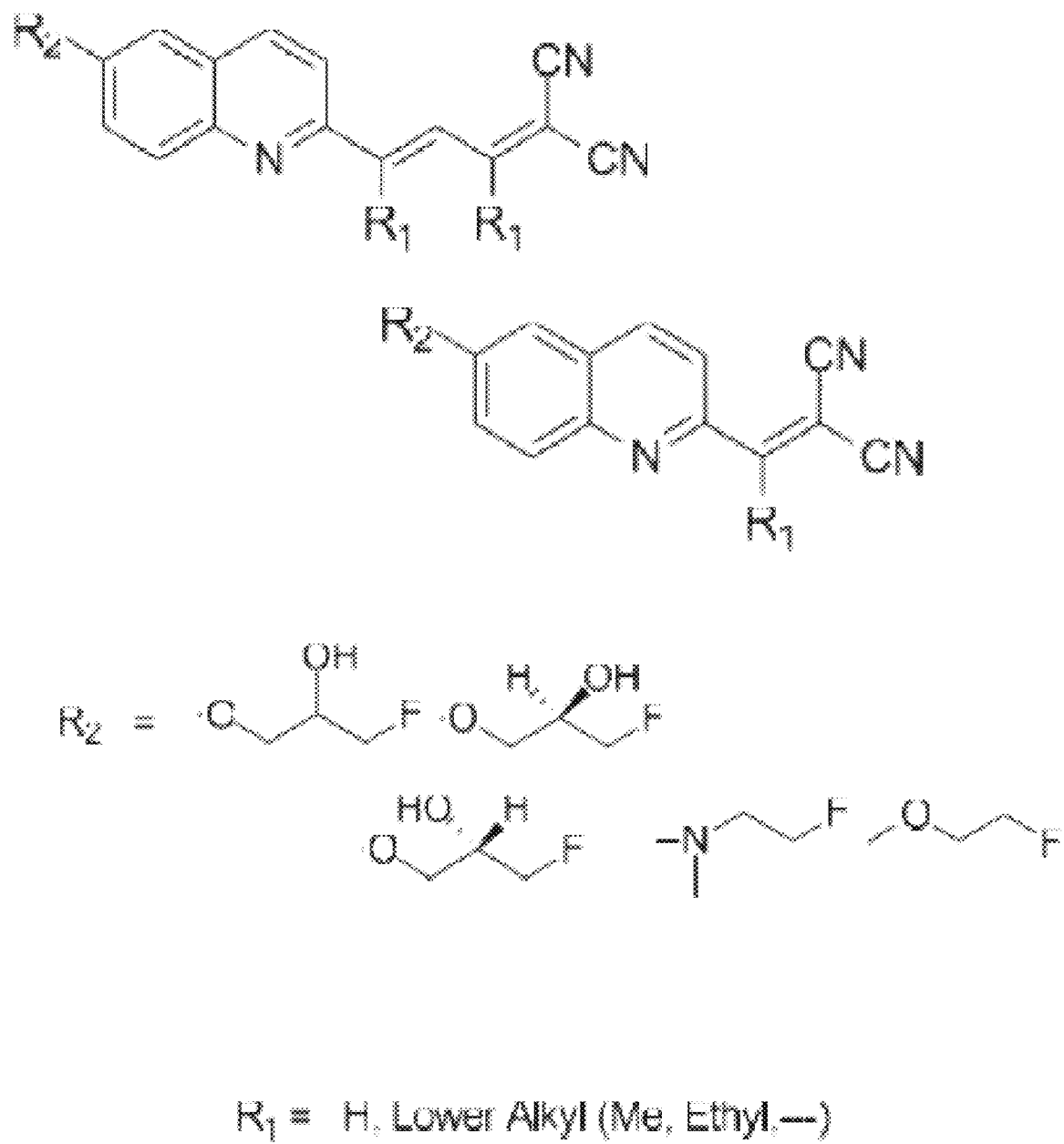
FIG. 4 depicts additional derivatives of the disclosure.

Selected analogues were assessed for their ability to interact with TDP 43 aggregates in vitro. Some derivatives show high enhancement in fluorescence following their incubation with TDP43 aggregates in vitro. Representative examples of some of the derivatives are shown in FIG. 3 and FIG. 4.

Figure 5:
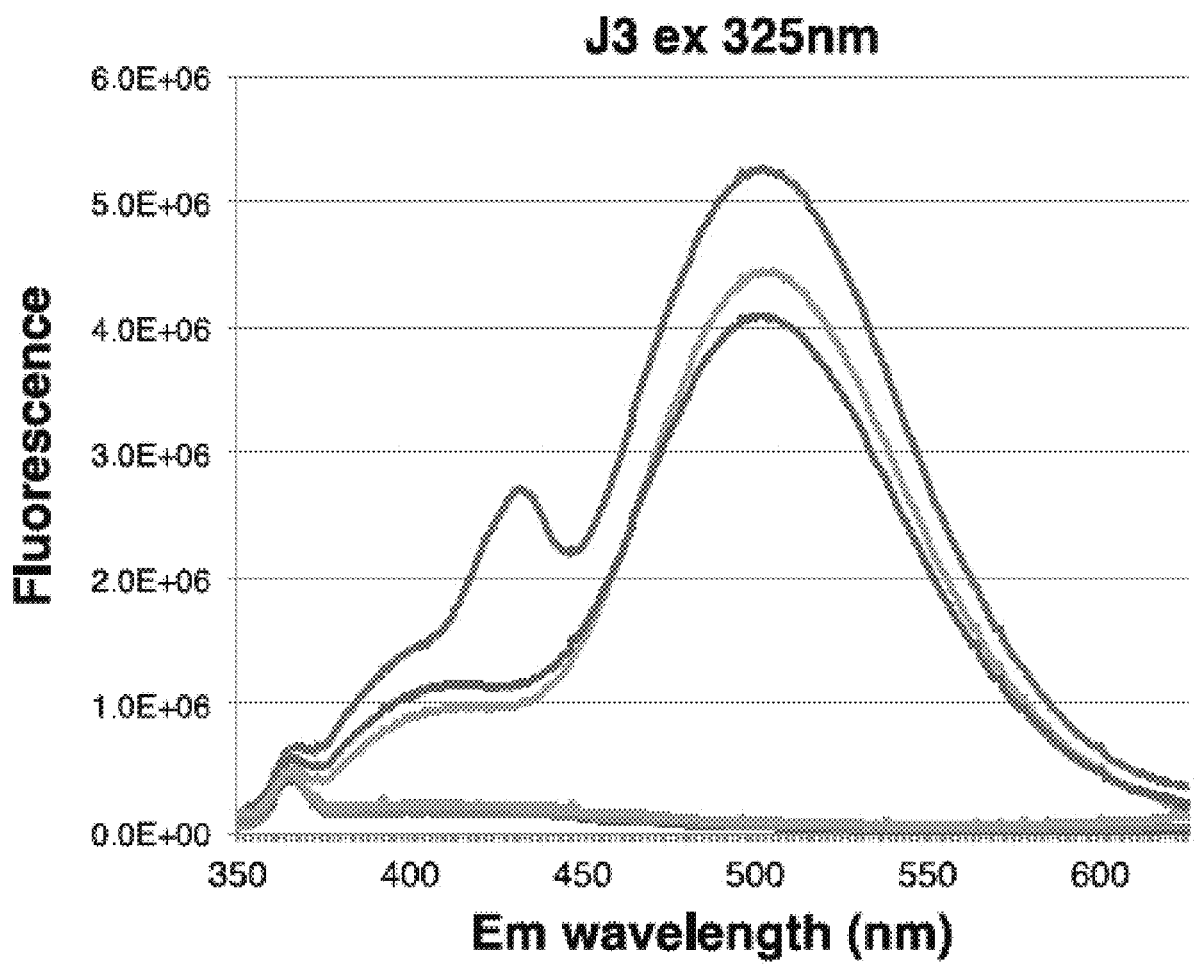
FIG. 5 depicts binding of fluorescently labeled compound to recombinant TDP-43 aggregates. Emission scanning analysis of the compound (SHAR165) upon excitation at 325 nm. SHAR165 (1 mM) and aggregates (0.2 mM) were incubated for 30 min at 25° C. in (125 mM NaCl, 50 mM Tris pH 8.0, 0.5% sucrose, 0.5% glycerol, 15 mM imidazole). Similarly, SHAR165 was also incubated with non-aggregated rTDP-43 as a control.

To assess ability of molecules to interact with TDP 43, their inherent fluorescent traits were employed. Selected molecules show enhancement in fluorescence upon incubation with TDP-43 aggregates (exemplified in FIG. 5) indicating their binding to the biomarker protein. Based upon these experiments, molecules were identified showing specificity for binding to TDP43 compared with its soluble form and certain leads were identified.

Figure 6:
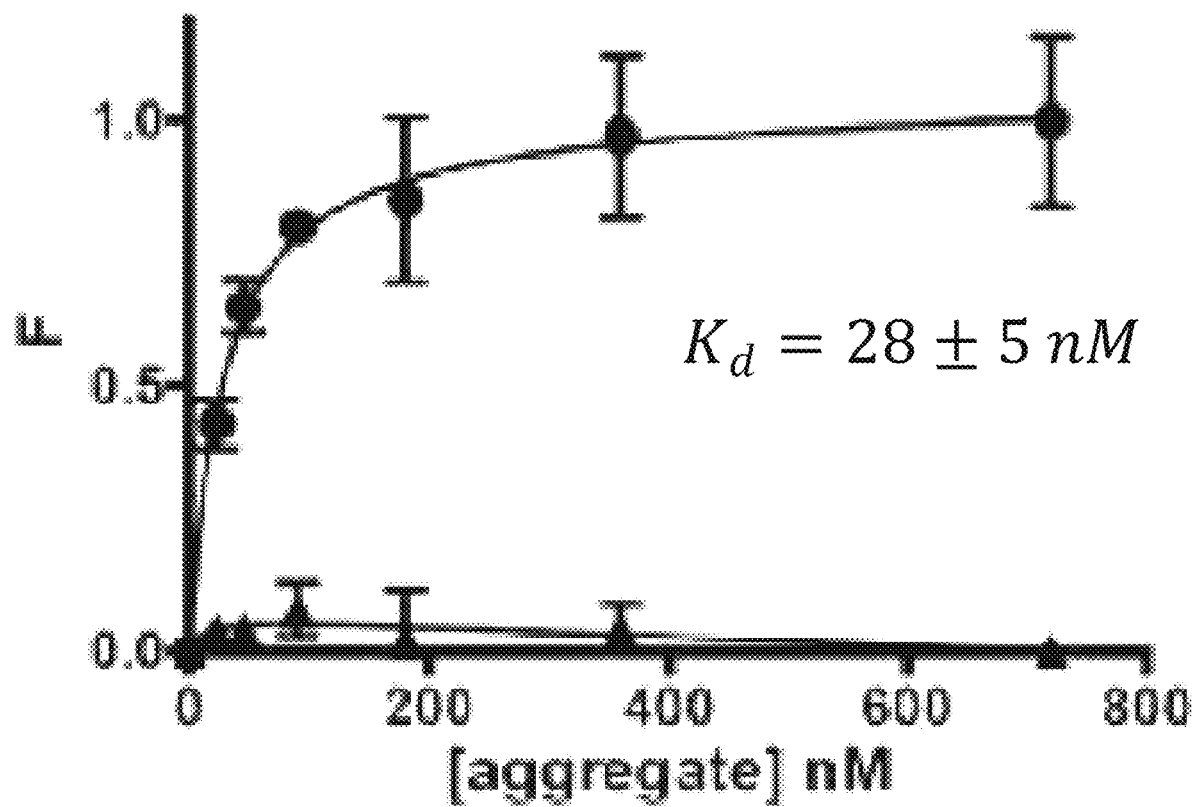
FIG. 6 depicts binding of SHAR165 to recombinant TDP-43 aggregates. The apparent dissociation constant for SHAR165 binding with TDP43 aggregates. Measurements of fluorescein 503 nm, excitation at 325 nm, are shown as the fractional change in fluorescence (F) at varying concentration of aggregates. $K_d$ was calculated using Graph Pad Prism v 6.0 (n=3, SEM shown). The effect of soluble TDP43 on SHAR165 indicated as triangles. Using single binding site model, $K_d$ was found to be 28±5 nM.

To assess binding affinity of one of the lead molecules, SHAR 165 was incubated as a function of concentration with a fixed concentration of TDP43 aggregates (200 nM) to determine the binding affinity. SHAR 165 (2) indicated a saturable binding affinity of 28±5 nM (FIG. 6).

Figure 7:
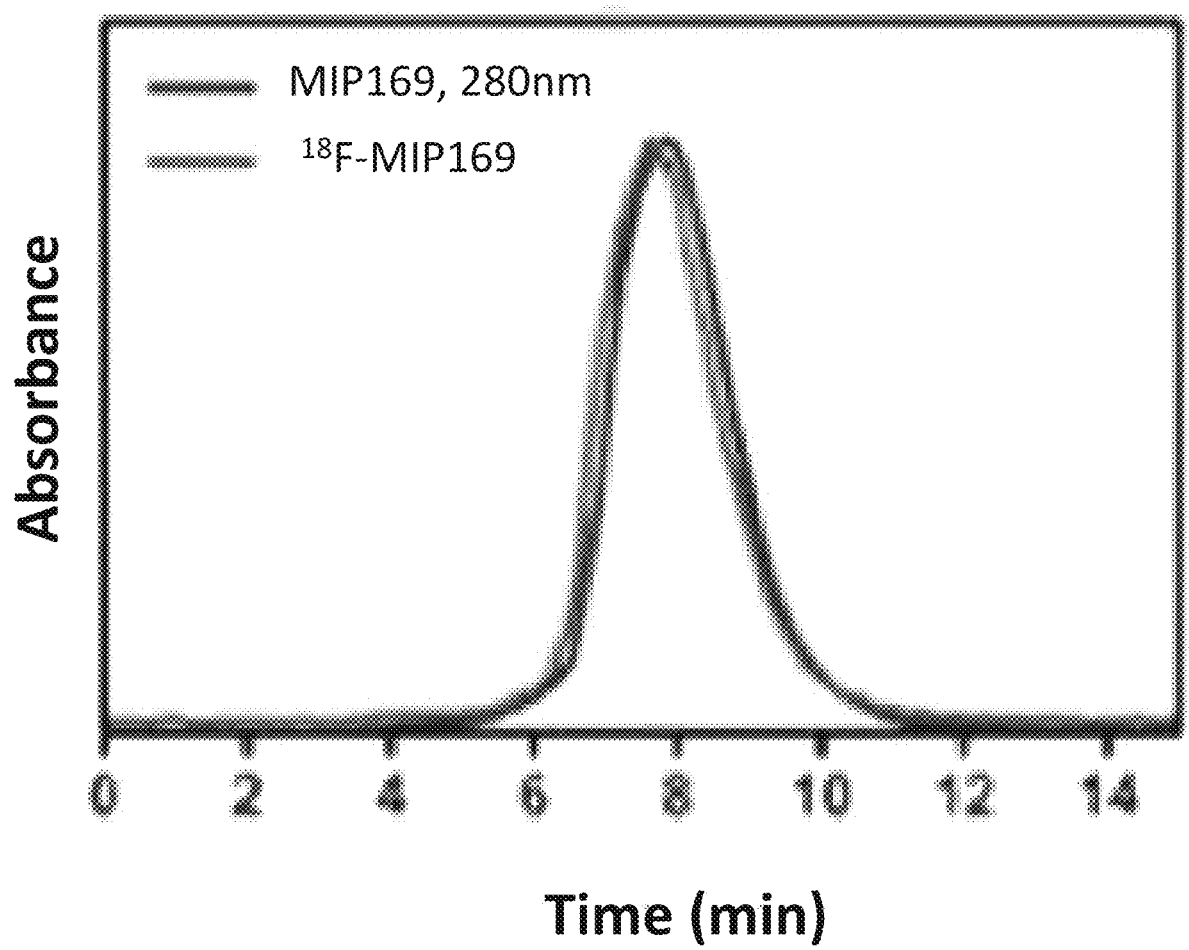
FIG. 7 depicts radio-HPLC data of purified $^{18}$F-SHAR165, the TDP-43-targeted probe (red), spiked with an unlabeled counterpart (blue).

To assess BBB permeability and pharmacokinetics of our lead agent (SHAR165), its PET counterpart $^{18}$F-SHAR165 was synthesized via standard nucleophilic substitution employing 2,2,2-kryptofix/$^{18}$F. Following completion of the reaction, the reaction mixture was diluted to 0.1% organic in water and loaded on an activated C-18 cartridge (Waters). The cartridge was washed with water (4×5 ml) and the residual activity was eluted with ethanol. Finally, $^{18}$F-SHAR165 was purified on C-18 column (Vydac) employing a gradient eluent mixture of ethanol and water using HPLC (Waters) system equipped with a radio-detector (Bioscans). The fraction eluting at Rt=8 min was collected, characterized by spiking with analytically characterized samples of unlabeled F-SHAR165 (FIG. 7) prior to injection on the radio-HPLC, and finally characterized fraction was concentrated, and reconstituted in saline to 5-10% ethanol for bioassays.

For in vivo imaging of TDP-43, the basic pharmacokinetic model in normal brains involves high initial penetration of the agent, followed by rapid clearance due to lack of a binding target. However, in TDP-43 brains, high initial penetration will be followed by regional cortical retention as the agent binds to TDP-43 thus leading to differential kinetics. To accomplish this objective, biodistribution studies of our lead $^{18}$F-SHAR165 were performed in normal FVB mice (n=3) for assessment of signal to noise ratios and clearance profiles. The uptake of $^{18}$F-SHAR165 in various organs was analysed in terms of percent injected dose per gram of the tissue (% ID/g). Preliminary biodistribution studies with HPLC purified $^{18}$F-SHAR165 in normal FVB mice (n=3) have revealed a transient brain uptake value of 3.12±0.27% ID/g and 1.20±0.01% ID/g, 2 min and 120 min post tail-vein injection, respectively, giving a 2 min/120 min clearance a ratio of 2.60, thus providing indirect evidence for its ability to cross the BBB, and permeate into brain in vivo. Additionally, the radiotracer clears rapidly from non-targeted critical tissues, such as liver and kidney (% ID/g Liver: 15.66±2.35 (2 min), 1.76±0.05 (120 min); Kidney: 12.47±1.57 (2 min), 1.74±0.04 (120 min). Off note, these clearance profiles could translate into favorable dosimetry profiles (MIRD analysis). Further biochemical validations are in progress.

What is claimed is:

1. A compound or a pharmaceutically acceptable salt thereof of formula (V):

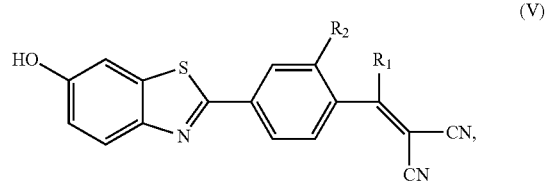

(V)

wherein:
R$_1$ is C$_1$-C$_4$ alkyl; and
R$_2$ is selected from the group consisting of hydrogen and a halogen.

2. The compound of claim 1, wherein the compound comprises a radionuclide selected from the group consisting of C-11, F-18, Br-75, Br-76, Br-77, I-123, I-124, I-125, and I-131.

3. The compound of claim 1, wherein the compound comprises a chelator which chelates a radionuclide or a metal atom selected from the group consisting of gallium-67, gallium-68, unlabeled gallium, indium-111, iron-52, iron-59, copper-62, copper-64, thallium-201, technetium-99m, technetium-94m, rhenium-188, rubidium-82, strontium-92, yttrium-86, yttrium-90, zirconium-86, zirconium-89, a paramagnetic metal ion, and a lanthanide metal ion.

4. The compound of claim 1, wherein the compound is a prodrug.

5. The compound of claim 1, wherein one or more atoms is replaced by a radioisotope of hydrogen, carbon, nitrogen, oxygen, sulfur, and halogens, such as $^2$H, $^3$H, $^{11}$C, $^{13}$C, $^{14}$C, $^{15}$N, $^{18}$O, $^{35}$S, $^{75}$Br, $^{76}$Br, $^{77}$Br, $^{18}$F, $^{36}$Cl, $^{131}$I, $^{125}$I, $^{124}$I, and $^{123}$I.

6. A complex comprising a compound of claim 1, or a pharmaceutically acceptable salt thereof, and a gold nanoparticle.

7. The complex of claim 6, wherein the gold nanoparticle is conjugated to the compound.

8. The complex of claim 7, wherein the gold nanoparticle is conjugated to the compound via a linker.

9. A pharmaceutical composition comprising a compound of claim 1.

10. The pharmaceutical composition of claim 9, wherein the pharmaceutical compositions is formulated as a solution, emulsion, suspension or dispersion in suitable pharmaceutical solvents or carriers or as pills, tablets, lozenges, suppositories, sachets, graees, granules, powders for reconstitution or capsules along with solid carriers used in various dosage forms.

11. A method of imaging distribution of TDP43 aggregates in a subject, the method comprising administering to the subject a composition comprising a compound or a pharmaceutically acceptable salt thereof of formula (V):

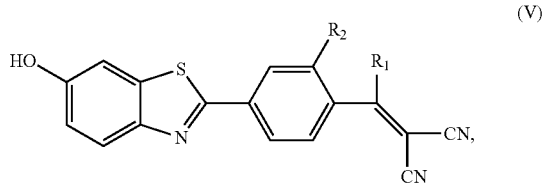

(V)

wherein:
$R_1$ is $C_1$-$C_4$ alkyl; and
$R_2$ is selected from the group consisting of hydrogen and a halogen, wherein the compound or pharmaceutically acceptable salt thereof comprises a radionuclide; and detecting the presence of a signal emitted from the compound.

12. The method of claim 11, wherein distribution of TDP43 aggregates is monitored in response to administration of a therapeutic agent.

13. The method of claim 12, wherein a therapeutic agent is selected from the group consisting of vitamin C, rapamycin, CDK, c-JNK inhibitors, and triptolide.

14. A method for detecting or monitoring a TDP43-mediated disorder, the method comprising administering to a subject an effective amount of a composition comprising a compound or a pharmaceutically acceptable salt thereof of formula (V):

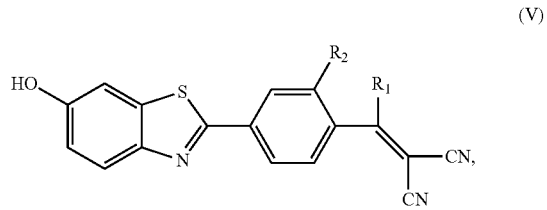

(V)

wherein:
$R_1$ is $C_1$-$C_4$ alkyl; and
$R_2$ is selected from the group consisting of hydrogen and a halogen wherein the compound or pharmaceutically acceptable salt thereof comprises a radionuclide; and detecting the presence of a signal emitted from the compound in the subject, wherein detection of signal above baseline indicates a TDP43-mediated disorder.

15. The method of claim 14, wherein the TDP43-mediated disorder is selected for the groups consisting of amyotrophic lateral sclerosis (ALS), frontotemporal dementia (FTD), and TDP43-mediated tumorigenicity of glioblastoma cells.

16. The method of claim 14, wherein progression is monitored in response to administration of a therapeutic agent.

17. The method of claim 16, wherein the therapeutic agent is selected from the group consisting of vitamin C, rapamycin, CDK, c-JNK inhibitors, and triptolide.

* * * * *